(12) United States Patent
Hudson et al.

(10) Patent No.: US 11,619,623 B2
(45) Date of Patent: Apr. 4, 2023

(54) INTEGRATED SAMPLE PROCESSING SYSTEM WITH VARIABLE WORKFLOWS

(71) Applicants: Beckman Coulter, Inc., Brea, CA (US); DH TECHNOLOGIES DEVELOPMENT PTE. LTD., Singapore (SG)

(72) Inventors: Aaron Hudson, Northborough, MA (US); Takayuki Mizutani, Edina, MN (US); Subhasish Purkayastha, Acton, MA (US); Thomas W. Roscoe, Prior Lake, MN (US)

(73) Assignees: Beckman Coulter, Inc., Brea, CA (US); DH Technologies Development PTE. LTD., Singapore (SG)

( * ) Notice: Subject to any disclaimer, the term of this patent is extended or adjusted under 35 U.S.C. 154(b) by 280 days.

(21) Appl. No.: 16/956,405

(22) PCT Filed: Dec. 19, 2018

(86) PCT No.: PCT/US2018/066561
§ 371 (c)(1),
(2) Date: Jun. 19, 2020

(87) PCT Pub. No.: WO2019/126363
PCT Pub. Date: Jun. 27, 2019

(65) Prior Publication Data
US 2021/0003551 A1   Jan. 7, 2021

Related U.S. Application Data

(60) Provisional application No. 62/607,685, filed on Dec. 19, 2017.

(51) Int. Cl.
*G01N 33/487* (2006.01)
*G01N 35/00* (2006.01)
(Continued)

(52) U.S. Cl.
CPC . *G01N 33/48792* (2013.01); *G01N 35/00871* (2013.01); *G01N 35/1095* (2013.01);
(Continued)

(58) Field of Classification Search
CPC ......... G01N 35/00871; G01N 35/0092; G01N 35/1095; G01N 33/487; G01N 33/48792;
(Continued)

(56) References Cited

U.S. PATENT DOCUMENTS 9,236,236 B2   1/2016  Dewitte et al.
10,627,395 B2*  4/2020  Wang ................ B01L 3/502738
(Continued)

FOREIGN PATENT DOCUMENTS

WO    WO-9801760 A2    1/1998
WO    WO-2017143182 A2  8/2017
WO    WO-2019126363 A1  6/2019

OTHER PUBLICATIONS

"International Application Serial No. PCT/US2018/066561, International Search Report dated Apr. 17, 2019", 4 pgs.
(Continued)

*Primary Examiner* — John H Le
(74) *Attorney, Agent, or Firm* — McAndrews Held & Malloy, Ltd.

(57) ABSTRACT

One embodiment of the invention is directed to a sample processing system for analyzing a biological sample from a patient. The sample processing system comprises: a plurality of analyzers comprising at least one mass spectrometer, wherein each analyzer in the plurality of analyzers is configured to acquire at least one measurement value corresponding to at least one characteristic of the biological sample; at least one data storage component which stores (i) a list of parameters for the plurality of analyzers, and (ii) at least two condition sets, which contain data associated with completing one or more test orders. The condition sets
(Continued)

contain data which differ by at least one variable; and a control system operatively coupled to the plurality of analyzers, and the at least one data storage component. The control system is configured to (i) determine which condition set of the at least two condition sets to use based on the determined condition set, (ii) determine which analyzer or analyzers of the plurality of analyzers to use to process each test order based on the determined condition set and one or more parameters from the list of parameters, and (iii) cause the determined analyzer or analyzers to acquire one or more measurement values for the biological sample.

20 Claims, 16 Drawing Sheets

(51) Int. Cl.
  *G01N 35/10* (2006.01)
  *G01N 35/04* (2006.01)
  *H01J 49/26* (2006.01)

(52) U.S. Cl.
  CPC .............. *G01N 2035/00356* (2013.01); *G01N 2035/00881* (2013.01); *G01N 2035/0444* (2013.01); *H01J 49/26* (2013.01)

(58) Field of Classification Search
  CPC .......... G01N 2035/00356; G01N 2035/00881; G01N 2035/0444; H01J 49/26
  USPC ........................................................ 702/19
  See application file for complete search history.

(56) References Cited

U.S. PATENT DOCUMENTS

| | | | |
|---|---|---|---|
| 2012/0004853 A1* | 1/2012 | Oeltjen | G01N 33/483 702/19 |
| 2014/0229955 A1* | 8/2014 | Holmes | G01N 35/0092 718/102 |
| 2015/0097113 A1 | 4/2015 | Campbell et al. | |
| 2015/0339438 A1 | 11/2015 | Oeltjen | |
| 2017/0160273 A1 | 6/2017 | Nogami et al. | |

OTHER PUBLICATIONS

"International Application Serial No. PCT/US2018/066561, Written Opinion dated Apr. 17, 2019", 4 pgs.

* cited by examiner

INTEGRATED SAMPLE PROCESSING SYSTEM WITH VARIABLE WORKFLOWS

CROSS-REFERENCES TO RELATED APPLICATIONS

This application is a U.S. National Stage Filing under 35 U.S.C. 371 from International Application No. PCT/US2018/066561, filed on Dec. 19, 2018 and published as WO 2019/126363 on Jun. 27, 2019, which application claims priority to U.S. Provisional Application No. 62/607,685 filed on Dec. 19, 2017, the contents of which are incorporated by reference in their entirety for all purposes.

BACKGROUND

Mass Spectrometry (MS) is an analytical technique used for determining the elemental composition of samples, quantifying the mass of particles and molecules, and elucidating the chemical structure of molecules. Various types of MS with high specificity, such as Liquid Chromatography (LC-MS), Gas Chromatography (GC-MS), and Matrix-Assisted Laser Desorption/Ionization/Time-Of-Flight (MALDI-TOF MS), are being increasingly used in clinical diagnostics. These MS techniques overcome many of the limitations of immunoassays (e.g. non-specific binding and cross reactivity of analytes) and offer many advantages).

To date, MS techniques have not found widespread clinical application due to challenges including sample preparation, online extraction, throughput, automation, laboratory information system interfacing, inter-instruments standardization and harmonization.

Further, the use of MS alone as a diagnostic tool has drawbacks. For example, MS is highly sensitive and can be more costly to run than other types of analyses. Further, because analytes need to be volatile in mass spectrometry, the number of sample preparation steps can be greater than other types of analyzers. Thus, MS may not be the optimal method for analyzing all types of biological samples under every circumstance.

Embodiments of the invention address these and other challenges, individually and collectively.

BRIEF SUMMARY

Some embodiments of the invention may include an integrated sample processing system that can include multiple analyzers, at least one of which is a mass spectrometer. Embodiments of the invention may also include a control system, which can be used to select an analyzer or combination of analyzers, one of which can be a mass spectrometer, to process a particular biological sample. The selection of which analyzer or combination of analyzers can depend upon a number of factors including the characteristics of the particular biological sample, one or more condition sets, analyzer parameters, and information in a test order for the biological sample.

One embodiment of the invention is directed to a sample processing system for analyzing a biological sample from a patient, the sample processing system comprising: a plurality of analyzers comprising at least one mass spectrometer, wherein each analyzer in the plurality of analyzers is configured to acquire at least one measurement value corresponding to at least one characteristic of the biological sample; at least one data storage component which stores (i) a list of parameters for the plurality of analyzers, and (ii) at least two condition sets, which contain data associated with completing one or more test orders, wherein the at least two of the condition sets contain data which differ by at least one variable; and a control system operatively coupled to the plurality of analyzers, and the at least one data storage component, and wherein the control system comprises a computer readable medium and a data processor. The computer readable medium comprises code, executable by the processor to cause the control system to (i) determine which condition set of the at least two condition sets to use based on the determined condition set, (ii) determine which analyzer or analyzers of the plurality of analyzers to use to process the one or more test orders based on the determined condition set and one or more parameters from the list of parameters, and (iii) cause the determined analyzer or analyzers to acquire one or more measurement values for the biological sample.

Another embodiment of the invention is directed to a method performed by a system comprising a plurality of analyzers comprising at least one mass spectrometer, at least one data storage component storing a plurality of condition sets, the condition sets in the plurality of condition sets differing by at least one variable, and a plurality of parameter lists for the plurality of analyzers, and a control system coupled to the plurality of analyzers, and the at least one data storage component. The method comprises determining, by the control system, in response to receipt of a test order to test a biological sample, one or more condition sets of the plurality of condition sets in the data storage component to use to complete the test order; determining, by the control system, an analyzer or analyzers from the plurality of analyzers to use to process the biological sample based on the one or more condition sets, and one or more parameters in the parameter lists in the plurality of parameter lists, the determined analyzer or analyzers including the at least one mass spectrometer; and causing, by the control system, the determined analyzer or analyzers of the plurality of analyzers to process the biological sample to determine one or more measurement values for the biological sample.

These and other embodiments of the invention are described in further detail below, with reference to the drawings.

DETAILED DESCRIPTION

Figure 1A:
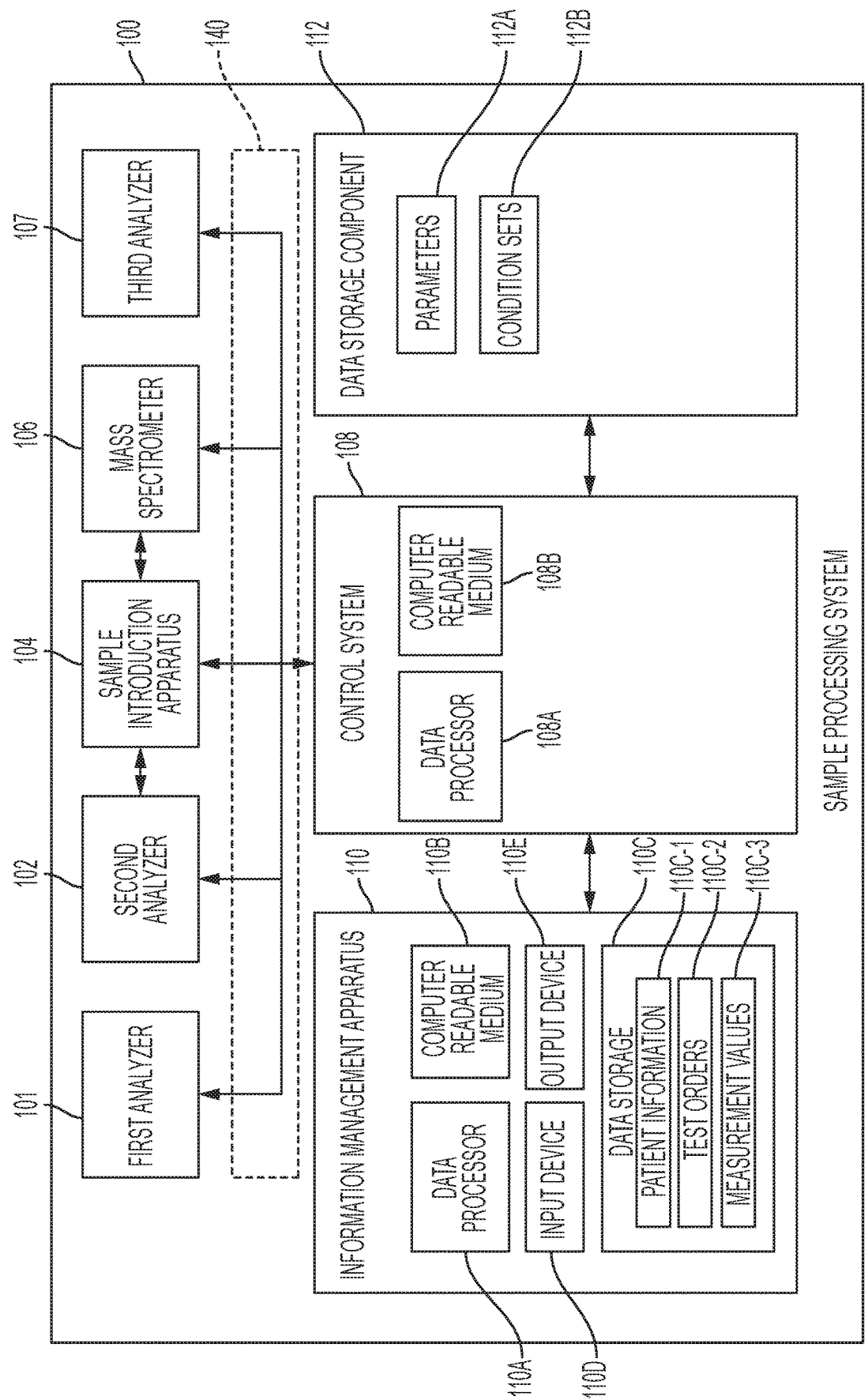
FIG. 1A shows a block diagram of an sample processing system according to an embodiment of the invention.

Embodiments of the invention may be used to detect the presence, absence, or concentration of analytes in biological samples. Biological samples such as biological fluids may include, but are not limited to, blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The term "analyzer" may include any suitable instrument that is capable of analyzing a sample such as a biological sample. Examples of analyzers include mass spectrometers, immunoanalyzers, hematology analyzers, microbiology analyzers, and/or molecular biology analyzers.

The term "measurement value" may include a specific value that is obtained in relation to an analysis of a biological sample. The measurement value may be determined by the one or more analyzers, or by an information management apparatus that obtains data from one or more analyzers. For example, a specific measurement value associated with a biological sample being analyzed by a mass spectrometer might be a specific mass to charge ratio that is observed for an analyte in the biological sample. Other types of measurement values may include fluorescence values. Measurement values may be in the form of raw data from an analyzer, or may be in form of data that is derived from raw data. In some cases, derived data can be more readily interpreted by system users than raw data. For example, fluorescent values from an analyzer may be converted to different numerical values such as concentration values. Either may be considered "measurement values."

A "characteristic" of a biological sample may include a property of the biological sample. The property of the sample may relate to the presence, absence, or quantity of components (e.g., organisms, proteins, etc.) in the sample. Characteristics of biological samples may also relate to disease conditions that might or might not be associated with the biological samples. For example, characteristics of biological samples may include whether or not those biological samples are associated with diseases such as Alzheimer's, cardiac disease, breast cancer, colorectal cancer, prostate cancer, ovarian cancer, lung cancer, pancreatic cancer, bladder cancer, and hepatocellular cancer. A characteristic of the biological sample may also pertain to a physical property of the biological sample, such as the color or appearance of the biological sample.

The term "parameter" may include a factor that relates to a condition of operation of an instrument such as an analyzer. Parameters may relate to detection ranges for different analyzers, types of measurement values obtainable by the analyzers, the costs of operating various analyzers, the availability (or scheduling) of analyzers, when calibrations were last completed, availability of personnel to perform manual sample preparation or operate analyzers; etc.

The term "condition set" may include one or more rules for handling specific types of biological samples. Each condition set may include a plurality of variables that may be associated with the one or more rules. Laboratory rules may include rules for handling samples, detection ranges needed to meet orders, etc. For example, a first condition set may include a first rule which states that if the patient is a female, then the patient's biological sample needs to be tested using a mass spectrometer. A second condition set may include a second rule that states if the patient is a male, then the patient's biological sample can be tested by using an immunoanalyzer or a mass spectrometer. Males generally have higher levels of testosterone than females, and these higher levels of testosterone can be detected using an immunoanalyzer or a mass spectrometer. On the other hand, because females have lower levels of testosterone, the lower levels of testosterone may not be detectable using an immunoanalyzer, but may be detectable by a mass spectrometer. In the latter case, a mass spectrometer may be the appropriate analyzer to use to analyze the female's biological sample. In another example, a condition set may specify that a mass spectrometer is to be used if the test order requests testing for a protein marker (the expression of which may correlate to a disease), a steroid (e.g., testosterone, estradiol, or progesterone), or for vitamin D. In yet other examples, condition sets may be used to specify if retest or reflex processing is to occur and on which analyzers for a particular biological sample, upon certain predetermined results from a primary analysis of the biological sample. Conditions sets could also be chosen based on the order; for example, if a clinician specifies that the analyte be determined with MS versus IA. Conditions sets could also be chosen based on a particular clinician; for example, an order submitted by an OBGYN could automatically include a pregnancy test.

The term "variable" may include a component of a rule in a condition set that can vary. For example, if a condition set includes a rule that states that if the patient is a male, then the patient's biological sample can be tested by using an immunoanalyzer or a mass spectrometer, then the variables that can be present in this condition set can be the sex of the patient (e.g., "male"), and the type of analyzer used (e.g., an "immunoanalyzer," and/or a "mass spectrometer"). Variables may pertain to characteristics of the patient from which the biological sample was obtained (e.g., the age, sex, ethnicity, pre-existing conditions of a patient, insurance coverage status of the patient), characteristics of the specific type of analyzers, specific types of analyzers, time periods for processing (e.g., process now or later), sample types (e.g., blood, urine, etc.) etc. A variable may also be determined by a laboratory according to factors that may be independent of the specific characteristics of a biological sample. For example, a laboratory provide a predetermined value that may be a variable that indicates a preference of analyzer use. This may be based upon the reliability or age of the analyzers.

The term "patient information" can include any suitable data related to a patient. Patient information may include, but is not limited to, at least the following types of information: demographic information (name, address, phone), biometric information, patient ID information (unique identifier used to tag samples), imaging information (x-ray, CT, MRI, US), surgical information, pharmaceutical information (e.g., specific drugs a patient is taking or should take and in what dose), billing information, EMR information, physician generated information (e.g., vital signs, observations, medical changes), and historical patient information (e.g., drug levels being monitored, chronic disease information, information about adverse drug reactions, etc.).

The term "test order" may include any suitable type of instruction for processing a biological sample. Exemplary test orders may include patient information associated with biological samples, the health care providers requesting the testing of the biological samples, tests to be performed on the biological samples (e.g., the detection of the presence or absence of specific analyte(s)), and the expected processing times (e.g., a STAT or short turnaround time sample) associated with the biological samples. Test orders may also specify specific types of analyzers to use to analyze the biological sample.

The term "analyte" may include a substance whose presence, absence, or concentration is to be determined according to embodiments of the present invention. Typical analytes may include, but are not limited to organic molecules, hormones (such as thyroid hormones, estradiol, testosterone, progesterone, estrogen), metabolites (such as glucose or ethanol), proteins, lipids, carbohydrates and sugars, steroids (such as Vitamin D), peptides (such as procalcitonin), nucleic acid segments, biomarkers (pharmaceuticals such as antibiotics, benzodiazepine), drugs (such as immunosuppressant drugs, narcotics, opioids, etc.), molecules with a regulatory effect in enzymatic processes such as promoters, activators, inhibitors, or cofactors, microorganisms (such as viruses (including EBV, HPV, HIV, HCV, HBV, Influenza, Norovirus, Rotavirus, Adenovirus etc.), bacteria (*H. pylori, Streptococcus*, MRSA, C. diff, Legionella, etc.), fungus, parasites (plasmodium, etc.), cells, cell components (such as cell membranes), spores, nucleic acids (such as DNA and RNA), etc. Embodiments of the invention can also allow for the simultaneous analysis of multiple analytes in the same class or different classes (e.g. simultaneous analysis of metabolites and proteins). In embodiments of the invention, the analysis of a particular analyte such as a biomarker may indicate that a particular condition (e.g., disease) is associated with a sample that contains the analyte.

The term "immunoassay" can be a laboratory method used to determine the amount of an analyte in a sample. It can be based on the interaction of antibodies with antigens, and because of the degree of selectivity for the analyte (either antigen or antibody), an immunoassay can be used to quantitatively determine very low concentrations of analyte in a test sample. "Immunoanalyzer" can include an instrument on which immunoassays have been automated. Various immunoanalyzers are commercially available including the DxI™ system (Beckman Coulter, CA), the ADVIA™ and CENTAUR™ systems (Siemens Healthcare, Germany), the COBAS™ system (Roche Diagnostic, Germany), the ARCHITECT™ system (Abbott, IL), the VITROS™ system (Ortho-clinical Diagnostic, NJ), and the VIDAS™ system (Biomerieux, France).

The term "mass spectrometer" may relate to an instrument which can measure the mass-to-charge ratios and relative concentrations of atoms and molecules. One example of a mass spectrometer makes use of the basic magnetic force on a moving charged particle. Basically, the instrument ionizes a sample and then deflects the ions through a magnetic field based on the mass-to-charge ratio of the ion. The mass spectrum can then be used to determine the elemental or isotopic signature of a sample, the masses of particles and of molecules, and to elucidate the chemical structures of molecules, such as peptides and other chemical compounds. Commercially available mass spectrometers can be categorized based on how they sector mass selection, including time-of-flight, quadrupole MS, ion traps (including 3D quadrupole, cylindrical ion traps, linear quadrupole ion traps, orbitraps), Fourier transform ion cyclotron resonance (FT-ICT), etc. Alternatively, they can be sectored based on ion source (laser desorption, matrix assisted laser desorption, thermal ionization, plasma, spark source, electrospray, etc.) or detectors (electron multipliers (such as Faraday cups and ion-to-photon detectors), inductive detectors, etc.). In a preferred embodiment, the mass spectrometer can be a triple quadrupole mass spectrometer.

One embodiment of the invention is directed to a method performed by a system comprising a plurality of analyzers comprising at least one mass spectrometer, and at least one data storage component. The plurality of analyzers may include multiple analyzers of the same type (e.g., at least two mass spectrometers), or different analyzers (e.g., one immunoanalyzer, one mass spectrometer, one hematology analyzer, etc.). The data storage component stores a plurality of condition sets, the condition sets in the plurality of condition sets differing by at least one variable. The data storage component also stores parameter lists for the plurality of analyzers. The system also includes a control system coupled to the plurality of analyzers, and the at least one data storage component. The control system can perform a method comprising determining in response to receipt of a test order to test a biological sample, one or more condition sets of the plurality of condition sets in the data storage component to use to complete the test order. Once the one or more condition sets are determined, the control system determines an analyzer or analyzers from the plurality of analyzers to use to process the biological sample based on the determined one or more condition sets and one or more parameters. The one or more determined analyzer or analyzers include the at least one mass spectrometer. The method also includes causing, by the control system, the determined analyzer or analyzers of the plurality of analyzers to process the biological sample to determine one or more measurement values for the biological sample.

Embodiments of the invention can include an integrated platform with a mass spectrometer (measuring mass) and one or more additional analyzers. In some embodiments, the mass spectrometer and the various analyzers can be present within the same housing. In other embodiments, the at least one mass spectrometer and the other analyzers can be in separate housings. In some embodiments, the analyzer can be an immunoanalyzer (typically detecting a label (chemiluminescent, electrochemiluminescent fluorescent, radioactive, isotope, DNA, etc. or label free system). Other types of analyzers may include hematology analyzers, microbiology analyzers, chemistry analyzers, urine analyzers, biochemical analyzers, and/or a molecular biology analyzers. When analyzing a biological sample, one or more of these types of analyzers, in any suitable combination, may be used to analyze the biological sample.

A hematology analyzer can be used to perform complete blood counts, erythrocyte sedimentation rates (ESRs), and/or coagulation tests. Automated cell counters sample the blood, and quantify, classify, and describe cell populations using both electrical and optical techniques.

A microbiology analyzer can function as a diagnostic tool for determining the identity of a biological organism. In some embodiments, a microbiology analyzer can identify an infecting microorganism. Such analyzers can use biochemicals in a plurality of small sample test microwells in centrifugal rotors that contain different substrates, or in multiwell panels, depending on the type of test being performed.

A molecular biology analyzer can be a device which can analyze a biological sample at its molecular level. An example of a molecular biology analyzer may include a nucleic acid analyzer such as a DNA analyzer.

A chemistry analyzer can run assays on clinical samples such as blood serum, plasma, urine, and cerebrospinal fluid to detect the presence of analytes relating to disease or drugs. A chemistry analyzer may use photometry. In photometry, a sample is mixed with the appropriate reagent to produce a reaction that results in a color. The concentration of the analyte determines the strength of color produced. The photometer shines light of the appropriate wavelength at the sample and measures the amount of light absorbed, which is directly correlated to the concentration of the analyte in the sample. Another analytical method used in a chemistry analyzer is the use of ion selective electrodes (ISE) to measure ions such as $Na^+$, $K^+$, $Cl^-$, and $Li^+$. An ISE is a sensor that determines the concentration of ions in a solution by measuring the current flow through an ion selective membrane.

Embodiments of the invention can include a system that uses two or more analyzers, one of which is a mass spectrometer. The analyzers may be used in any suitable combination to process biological samples. In some embodiments, a sample staging apparatus can also be present in the system. The sample staging apparatus may be used to present samples or portions of samples to the analyzers that are used to process the biological sample.

The system also comprises a control system that can control the mass spectrometer, the various analyzers, and the sample staging apparatus. The sample staging apparatus can be separate from or shared with any of the analyzers in the system. In some cases, the sample staging apparatus may include a track or transport system that can transport or route sample containers or sample vessels within the system. The system according to embodiments of the invention can be capable of (1) independent analysis by one or more analyzers and/or (2) serial or parallel analysis by one or more analyzers. Serial analysis can include either retesting (e.g., same analyte tested on both analyzers) or reflex testing (e.g., a first analyte is tested on one analyzer (typically the immunoanalyzer) and a second or more analyte(s) are tested on the other analyzer (typically the mass spectrometer)).

In some cases, a single sample staging apparatus is used for all of the analyzers (e.g., including the mass spectrometer). In other embodiments, sample preparation stations are present for each of the analyzers, and a common sample staging apparatus is not needed in all embodiments. Each sample preparation station comprises a means (or device) for aliquoting the sample (such as an aliquoter), and means for holding at least one reagent pack comprising the reagents needed for the various analyzers. In some embodiments, the sample preparation station comprises a means for holding different reagent packs for the different types of analyzers in the system.

In some embodiments, the system may include a sample introduction system that allows for the direct transfer of a biological sample between two analyzers. The sample introduction system for introducing a sample to one or more of the analyzers can be fluidically linked to at least one of the sample preparation systems in one of the other analyzers or outside of the one or more analyzers. In some embodiments, the sample introduction system may include direct flow injection, the use of a trap and elute system (e.g., a trap and elute system which includes 2 pumps and a 6-port switching valve), the use of an open port apparatus such as an open port probe.

The control system according to embodiments of the invention can perform a number of additional functions. For example, the control system can cause the sample processing system to process a primary sample and provide results regarding the presence, absence, or quantity of a particular analyte in the primary sample. The control system can further cause the sample processing system to process a second sample and provide results regarding the presence, absence, or quantity of one or more analytes in the second sample. The first and second samples can be processed by the same analyzer (e.g., an immunoanalyzer or a mass spectrometer) or by different analyzers (e.g., an immunoanalyzer and a mass spectrometer). The control system can control what reagent packs are used to process samples (e.g. if mass tags are desirable to use, the control system could direct the sample preparation system to use a first reagent pack with the first sample aliquot and a different, second reagent pack containing the mass tags with the second sample aliquot).

In some embodiments of the invention, a mass analysis can be performed after initial testing of the sample using one type of analyzer such as an immunoanalyzer. That is, the mass spectrometer can be used to perform reflex testing of a sample that was previously processed by a different analyzer or set of analyzers including an immunoanalyzer. The systems and methods according to embodiments of the invention also provide for the ability to perform automated reflex testing based upon predetermined criteria using a control system running intelligent software. Based on whether the results from the primary immunoassay meet certain criteria, the software can determine if the sample should be retested by the same analyzer (e.g., the immunoanalyzer) or reflex tested by the mass spectrometer. Since the primary sample can still be "on-deck" in the immunoanalyzer, the sample preparation for the mass spectrometric analysis assay can be initiated if the control system determines that a retest or a reflex test is desirable or necessary. The sample processing system can advantageously have reagent cartridges for various the detection processes associated with the various analyzers.

In some embodiments, two, three, or more aliquots of the primary sample can be prepared for the different analyses performed by the different analyzers including the mass spectrometer. This may involve separating the biological sample into multiple aliquots and providing the multiple aliquots into multiple sample retention vessels, the multiple sample retention vessels used in respective analyzers in the two or more analyzers. Aliquot preparation can occur in a sample staging apparatus, or it may occur within one of the analyzers.

In some embodiments, where the first analyzer used is an immunoanalyzer, after eluting an analyte originally present in the primary sample from an antibody bound to a magnetic particle, the eluant containing the analyte can be characterized as a processed sample aliquot, since it is derived from an original sample aliquot. The processed sample aliquot can then be analyzed by the mass spectrometer. Primary samples and processed sample aliquots, and any additional sample aliquots can be temporarily held in a sample storage unit (optionally, a chilled unit) while the control system determines if mass spectrometric analysis is needed.

When the control system determines that a retest or reflex process is necessary or desirable (due to the outcome of the analysis of a particular condition set), and the sample needs to be processed by the mass spectrometer, either a primary sample or a processed sample aliquot can be used. A retest process may be necessary or desirable if a primary analysis is viewed by the control system or other entity as being inconclusive, inadequate by itself, or incomplete. A reflex test may be necessary or desirable if the primary analysis of a first analyte indicates that further testing of one or more other analytes is desirable.

Embodiments of the invention can provide simplified workflows from sample preparation to a final analysis result with multiple options to improve the sensitivity, specificity and accuracy of the sample analysis process. With respect to the use of a sample introduction apparatus that is used to transfer a sample from an immunoanalyzer to a mass spectrometer, embodiments of the invention can eliminate the need for utilizing centrifugation and/or HPLC (high pressure liquid chromatography) prior to any mass spectrometer analysis. In some embodiments, no centrifuge and no HPLC apparatus is present in the sample processing system.

As noted above, the sample processing system can utilize a mass spectrometer to analyze a biological sample. The sample can be prepared for a mass spectrometric analysis in any suitable manner. For example, a first example sample preparation procedure that can be performed by the sample preparation system may include immunopurification of a target analyte from a primary sample using a monoclonal or polyclonal antibody attached to a paramagnetic particle. In an immunopurification process, after the analyte is captured by the antibody, any unbound molecules are washed away in a washing process. In a subsequent elution step, the analyte is subsequently released from the antibody using a buffer and the eluant. The eluant containing the "purified" target can be characterized as a processed sample aliquot, which is then collected and analyzed by the mass spectrometer.

The antibody that is typically used in the immunopurification process can be replaced by alternatives, e.g. aptamers, nanoparticles, binding proteins, etc. The immunocapture reagent can be designed to capture a specific analyte or a specific panel of analytes, e.g., drug panel or endocrine panel, etc. In embodiments of the invention, an MRM (multiple reaction monitoring) workflow using a triple quadrupole mass spectrometer, where specific parent to daughter ion transitions are present for each analyte, can be utilized to accurately analyze the specific analytes in the panel. In case there are no differentiating transitions in tandem mass spectrometry or $MS^2$ (typically in case of isomers or isobars), a unique transition in $MS^3$ may be utilized to differentiate between them.

In a second exemplary procedure performed in the sample preparation system, protein precipitation is used to separate proteins from small molecules. The proteins in a sample aliquot are precipitated using a precipitation reagent, after which the precipitated proteins are bound to paramagnetic beads. The proteins bound to the beads can be physically separated from a supernatant using a magnetic washing process. The supernatant liquid, which can be characterized as a processed sample aliquot, can be collected and transferred to the mass spectrometer for analysis. Drug classes for definitive or stand-alone testing can be analyzed using this workflow.

In some embodiments, mass spectrometric reagents such as mass tags (e.g., Amplifex™ mass tags) can be used during the sample preparation process to enhance signals and improve sensitivity. Mass tags are typically designed to react specifically with functional groups common to a specific class of analytes, e.g., keto functionality present in steroid class or diene functionality present in the Vitamin D class, etc. Mass tags can influence fragmentation of the molecule to yield specific fragments to provide unique transitions, which can lead to more accurate results. In some cases, the differential mobility of ions in the gas phase may also be used to separate isomeric or isobaric compounds. Reagents such as this can be used with the second sample aliquot that will be processed for a mass spectrometric analysis.

Mass tags can be designed to provide accuracy in a number of ways. First, mass tags may be used to modify the differential mobility of the tagged ions (target analyte and interfering compounds) in the gas phase and simplifying their separation based on differences in their mobility properties. Separating isomeric/isobaric compounds (referred to as interfering compounds) before detection can help to improve the accuracy of any analysis results. Second, mass tags can also provide signal enhancement of the target analyte to improve sensitivity. Third, mass tags can influence fragmentation of the tagged molecules to help differentiate analytes and interfering compounds.

In embodiments of the invention, an internal standard of the analyte(s) can be added to the sample prior to analysis by a mass spectrometer. The internal standard can be an isotopic version of the analyte(s) and can compensate for losses during the sample preparation process. The ratio of the internal standard to the analyte peak can be used for quantitation. Quantitation can be performed using an external calibration curve, if desired.

In addition, embodiments of the invention can use universal trap columns and solvents, and a universal mass spectrometry source, which can make automation less complex. A universal trap column and source can work for most assays and will not require switching between different assays. The software in the control system can indicate when the life of the universal trap column is up and needs replacement. Yet other embodiments of the invention may utilize LC (liquid chromatography) columns.

FIG. 1A shows a high level block diagram of a sample processing system 100 according to an embodiment of the invention. The sample processing system 100 comprises a plurality of analyzers. The plurality of analyzers may include a first analyzer 101, a second analyzer 102, a third analyzer 107, and a mass spectrometer 106. The mass spectrometer 106 is a type of analyzer. Although one mass spectrometer is shown for purposes of illustration, it is understood that more than one mass spectrometer may be present in the sample processing system 100. Further, although three analyzers 101, 102, 107 other than the mass spectrometer 106 are illustrated in FIG. 1A, it is understood that there can be fewer than three additional analyzers, or more than three analyzers in other embodiments of the invention.

A control system 108 may be operatively coupled to the three analyzers 101, 102, 107 other than the mass spectrometer 106, as well as an information management apparatus 110 and a data storage component 112. Input/output interfaces may be present in each of these devices to allow for data transmission between the illustrated devices and any external devices.

In this example, a sample introduction apparatus 104 may be disposed between the mass spectrometer 106 and the second analyzer 102. The sample introduction apparatus 104 may be physically and/or operationally coupled to the analyzer 102 and the mass spectrometer 106. The sample introduction apparatus 104 may serve to transfer processed samples or sample aliquots directly from the analyzer 102 to the mass spectrometer 106. For example, the sample introduction apparatus configured to transfer a first or second processed sample aliquot from the analyzer 102 to the mass spectrometer 106. Although the sample introduction apparatus 104 is shown as being present between the second analyzer 102 and the mass spectrometer 106, it may alternatively or additionally be configured to transfer a biological sample directly between any of the analyzers in the sample processing system 100.

In one example, the second analyzer 102 may include a number of sample aliquot processing apparatuses to form processed sample aliquots for analysis. Such processing apparatuses may process a sample or sample aliquot in any suitable manner. Examples of sample aliquot processing apparatuses include reagent addition stations (e.g., reagent pipetting stations), sample pipetting stations, incubators, wash stations (e.g., a magnetic wash station), sample storage units, etc. The plurality of sample aliquot processing apparatuses are capable of processing the first sample aliquot to form the first processed sample aliquot, and capable of processing the second sample aliquot to form the second processed sample aliquot. A "processed sample aliquot" may include a sample aliquot that is processed any suitable number of times by any suitable number of processing apparatuses.

The control system 108 can control and/or transmit messages to the first, second, and third analyzers 101, 102, and 107, the sample introduction apparatus 104, and/or the mass spectrometer 106. The control system 108 may comprise a data processor 108A, and a non-transitory computer readable medium 108B and a data storage 108C coupled to the data processor 108A. The non-transitory computer readable medium 108B may comprise code, executable by the processor 108A to perform the functions described herein. Although the control system 108 (as well as the information management apparatus 110) is depicted as a single entity in FIG. 1A, it is understood that the control system may be present in a distributed system or in a cloud-based environment.

The data processor 108A may include any suitable data computation device or combination of such devices. An exemplary data processor may comprise one or more microprocessors working together to accomplish a desired function. The data processor 108A may include a CPU that comprises at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

The computer readable medium 108B and the data storage 108C may be any suitable device or devices that can store electronic data. Examples of memories may comprise one or more memory chips, disk drives, etc. Such memories may operate using any suitable electrical, optical, and/or magnetic mode of operation.

The computer readable medium 108B may comprise code, executable by the data processor 108A to perform any suitable method. For example, the computer readable medium 108B may comprise code, executable by the processor 108A, to cause the sample processing system 100 perform a method including determining, in response to receipt of a test order to test a biological sample, one or more condition sets of the plurality of condition sets in the data storage component to use to complete the test order; determining an analyzer or analyzers from the plurality of analyzers to use to process the biological sample based on the one or more condition sets, and one or more parameters in the plurality of parameter lists, the determined analyzer or analyzers including the at least one mass spectrometer; and causing the determined analyzer or analyzers of the plurality of analyzers to process the biological sample to determine one or more measurement values for the biological sample.

The system 100 may also comprise a data storage component 112. The data storage component 112 may store parameters 112A and condition sets 112B. The data storage component 112 may be internal or external to the control system 108 or the information management apparatus 110. The data storage component 112 may include one or more memories including one or more memory chips, disk drives, etc. The data storage component 112 may also include a conventional, fault tolerant, relational, scalable, secure database such as those commercially available from Oracle™ or Sybase™.

The parameters 112A in the data storage component 112 may include any factor that relates to a condition of operation of an instrument such as an analyzer. Parameters may relate to detection ranges for different analyzers, types of measurement values obtainable by the analyzers, the availability of the analyzers, the cost of performing an operation on an analyzer, etc. The parameters 112A may include static (e.g., detection capabilities of analyzers) and/or dynamic information (e.g., the current availability of an analyzer or when it will be available). With respect to dynamic information, the control system 108 may receive data from each of the analyzers 101, 102, 107, and the mass spectrometer 106 on a regular basis to provide updated parameters 112A. For example, signals may be provided to the various analyzers 101, 102, 107 or the mass spectrometer 106 indicating that they are idle or busy and this information may be provided by the control system 108 to the data storage component 112.

The condition sets 112B may include a set of rules for handling specific types of biological samples. Each condition set may include a plurality of variables. Laboratory rules may include those for handling samples, detection ranges needed to meet order, etc. As noted above, condition sets may include one or more rules that can be used to determine which analyzer or combination of analyzers to select to process a biological sample. The rules may be associated with the biological sample and/or may incorporate data unrelated to the specific biological sample.

In some embodiments, condition sets 112 may include one or more rules that will cause the control system 108 to select the mass spectrometer 106 to analyze the biological sample. For example, a test order to test for a presence of at least one drug or metabolite thereof or both in a biological sample may be received by the sample processing system 100. At least one condition set of the at least two condition sets may comprise a rule that causes the control system to select the mass spectrometer from the plurality of analyzers in the system to analyze the biological sample for the drug or the metabolite. The at least one drug may include a therapeutic drug, a drug of abuse, and/or an immunosuppressant drug.

The sample processing system 100 may also comprise an information management apparatus 110. The information management apparatus 110 may be coupled to the control system 108, and may be configured to (i) store patient information, (ii) receive one or more test orders for the biological sample, and (iii) receive the one or more measurement values of the biological sample from the plurality of analyzers 101, 102, 107, including the mass spectrometer 106.

The information management apparatus 110 may comprise a data processor 110A and a non-transitory computer readable medium 110B. The computer readable medium 110B may comprise code for causing the data processor 110A to receive from the analyzer or analyzers 101, 102, 106, 107, the one or more measurement values for the biological sample, compare the one or more measurement values to patient information 110C-1 stored in a data store in a data storage 110C, and provide an output after comparing. The patient information 110C-1 in the information management apparatus 110 may be a patient information repository. The data processor 110A and the non-transitory computer readable medium 110B may be of the same or different type than the data processor 108A and the computer readable medium 108B in the control system 108.

The information management apparatus 110 may also comprise a data storage 110C, which may store patient information 110C-1, test orders 110C-2, and measurement values 110C-3. The information management apparatus 110 may also include one or more input devices 110D and output devices 110E. Input devices may include touchscreens, keyboards, pointers, microphones, etc. Output devices 110E may include speakers, displays, and tactile devices.

In some embodiments, the information management apparatus 110 may be configured to compare the presence or absence of a drug or metabolite in a biological sample, as determined by the mass spectrometer 106 or any of the other analyzers 101, 102, 107 to patient information 110C-1 in the data storage 110C. As a result of this comparison, an output may be provided by the information magnement apparatus 110 via an output device such as a display coupled to the data processor 110A.

The output may be of any suitable type. For example, the output may relate to a report that combines the measurement values from the analyzers 101, 102, 107, and/or the mass spectrometer 106 with patient information 110C-1 such as the name of the patient or medical record number of the patient. In other embodiments, the output may include the result of a comparison of any or proposed medications of the patent to any measurement values to the measurement values. In yet other embodiments, the output might be a diagnosis or recommendation based upon the measurement values obtained from the analyzers and the patient information 110C-1. In other embodiments, an output from the analyzers 101, 102, 107 or the information management apparatus 110 may be in form of images (e.g., a hematalogy analyzer could output an image of a cell).

In some embodiments, the information management apparatus 110 may include a laboratory information system (LIS), a hospital information system (HIS), and middleware. The analyzers 101, 102, 107, and the mass spectrometer 106 may be connected directly to the LIS over a network. Data (e.g., measurement values) generated by analyzers 101, 102, 107, and the mass spectrometer 106 can be transmitted to the LIS or HIS. A middleware hub may be inserted into this data flow on the communication path between the analyzers 101, 102, 107, and the mass spectrometer 106. The LIS, with an information system interface, allows for communications between the LIS and the middleware hub. In some implementations, the middleware hub may provide additional instructions to the analyzers 101, 102, 107, and the mass spectrometer 106 in order to create, cancel, or modify test orders for the analyzers 101, 102, 107, and the mass spectrometer 106 to execute. In some embodiments, the middleware hub may include the control system 108 or may include software running on the control system 108.

The sample processing system 100 may also include an optional sample staging apparatus 140 that may be operatively coupled to the control system 108, as well as the first analyzer 101, the second analyzer 102, the sample introduction apparatus 104, the mass spectrometer 106, and the third analyzer 107. The sample staging apparatus 140 may include any number or type of device that is needed to prepare or transport biological samples to the first analyzer 101, the second analyzer 102, the sample introduction apparatus 104, the mass spectrometer 106, and/or the third analyzer 107.

Figure 1B:
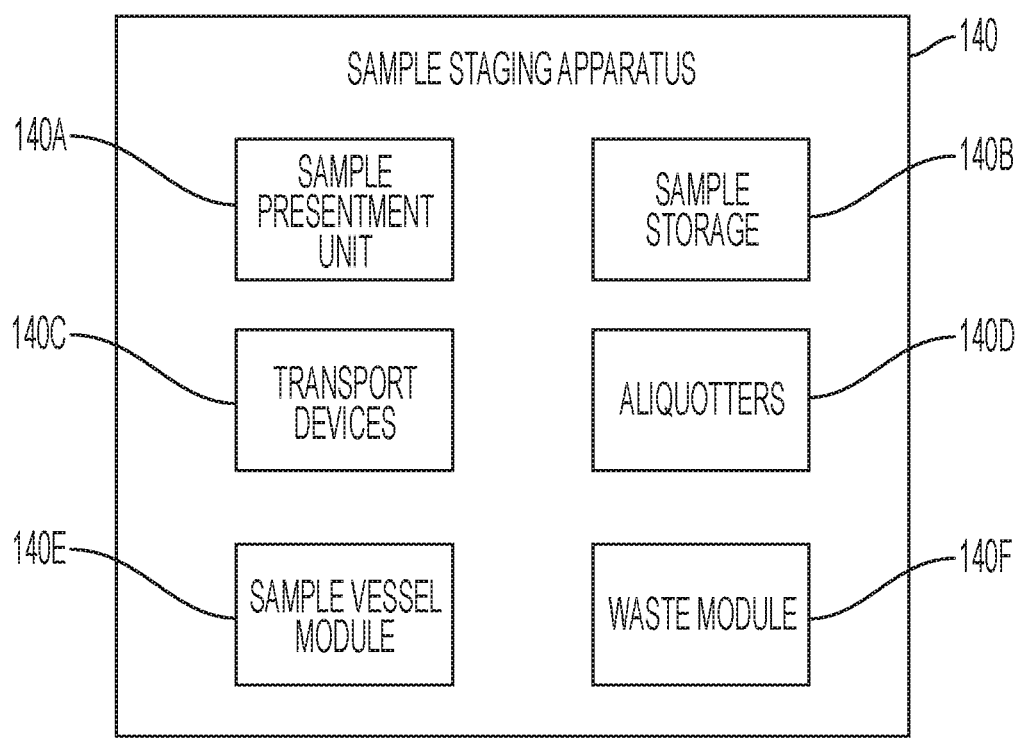
FIG. 1B shows a block diagram of a sample staging apparatus according to embodiment of the invention.

FIG. 1B shows a block diagram of some components that may be in an exemplary sample staging apparatus 140. The sample staging apparatus 140 may include a sample presentment unit 140A for receiving sample tubes with biological samples, a sample storage unit 140B for temporarily storing sample tubes or sample retention vessels, and various transport devices 140C. The transport devices 140C may be for transporting sample tubes or sample retention vessels to and from the first analyzer 101, the second analyzer 102, the sample introduction apparatus 104, the mass spectrometer 106, and/or the third analyzer 107. Examples of transport devices may include conveyors, sample tracks, pick and place grippers, laboratory transport elements that can move independently (e.g., pucks), and other tube conveying mechanisms. The sample staging apparatus 140 may also include one or more aliquotters 140D for aliquotting biological sample from a sample tube to a sample retention vessel, and a sample vessel module 140E for holding empty retention vessels. The sample stating apparatus 140 may also include a waste module 140F for collecting waste or spent sample retention vessels or sample tubes.

Figure 1C:
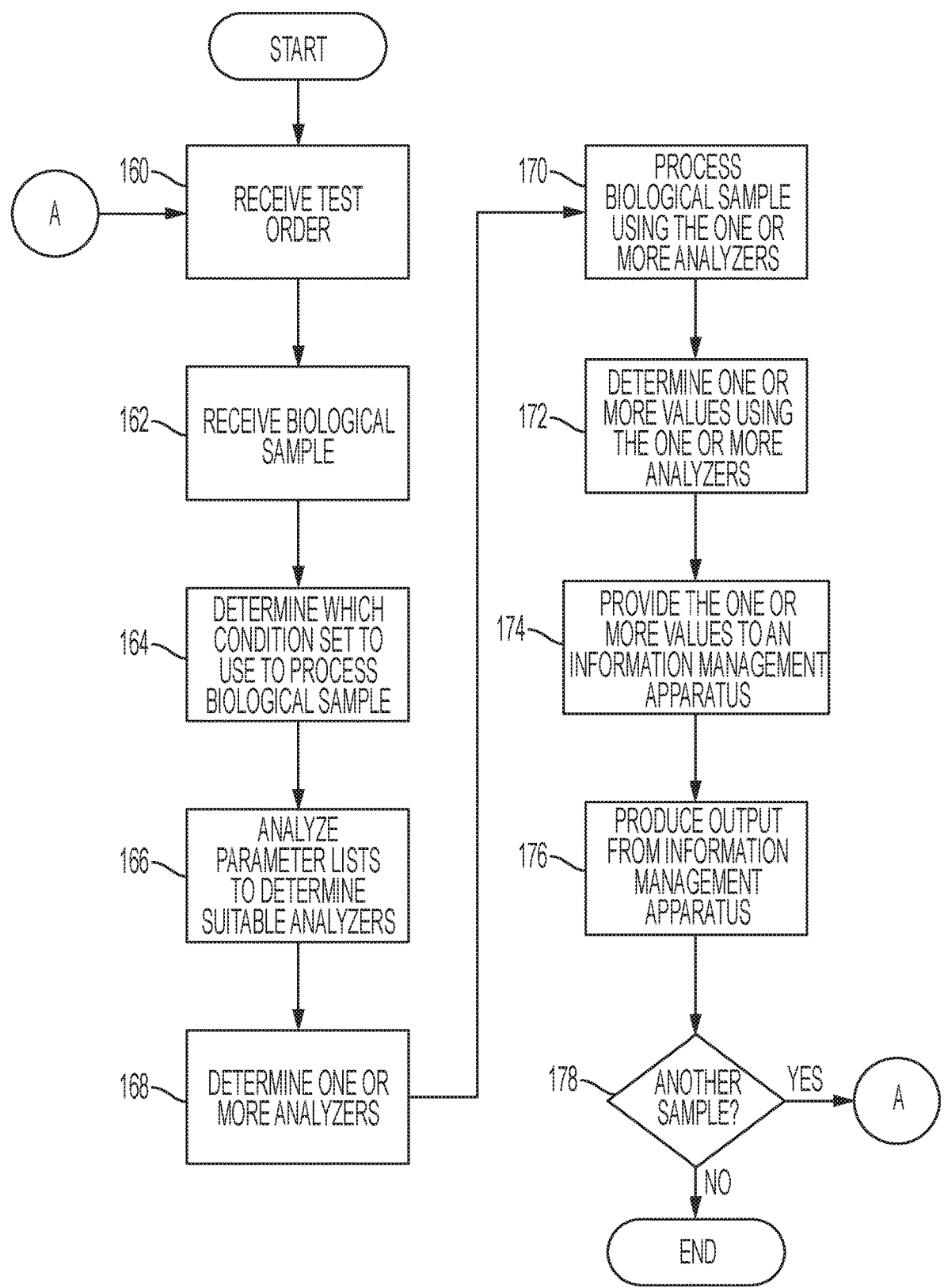
FIG. 1C shows a flowchart illustrating a method according to embodiment of the invention.

FIG. 1C shows a flowchart illustrating a method according to an embodiment of the invention. In one embodiment of the invention, the method is performed by a sample processing system. The sample processing system includes a plurality of analyzers comprising at least one mass spectrometer, at least one data storage component storing a plurality of condition sets, the condition sets in the plurality of condition sets differing by at least one variable, and a plurality of parameter lists for the plurality of analyzers. The sample processing system also includes a control system coupled to the plurality of analyzers, and the at least one data storage component.

In step 160, a test order is received at the information management apparatus 110 of the sample processing system 100. The test order may be stored with other test orders 110C-2 in the data storage 110C in the information management system 110. The test order may be received by the information management apparatus 110 via an input device 110D in the information management apparatus 110.

In step 162, before or after step 160, a biological sample is received by the sample processing system 100. In some embodiments, the biological sample is received at the sample staging apparatus 140. The biological sample may be present in a sample tube and placed in the sample presentment unit 140A of the sample staging apparatus 140.

In step 164, the control system 108 determines, in response to receipt of the biological sample and the test order, one or more condition sets from a plurality of condition sets stored in the data storage component 112 to use to process the biological sample. As an illustration, the test order may request that a biological sample of blood be tested for the presence or amount of a particular drug of abuse. The test order may further request that the test be performed within a particular period of time, and that the test result have a predetermined degree of confidence. An exemplary condition set may be selected, based upon the information in the test order and information relating to the biological sample. For example, the control system 108 may determine that if the biological sample is blood, and if the predetermined confidence level is to be achieved, then the second analyzer 102 which may be an immunoanalyzer, and the mass spectrometer 106 are selected to analyze the biological sample. Any other analyzers that may be suitable to achieve the end result may also be included in the list of candidate analyzers.

In step 166, before or after step 164, the control system 108 analyzes the parameter lists relative to the information in the test order to determine the appropriate analyzer or combination of analyzers that would be suitable to process the biological sample according to the test order. The control system 108 may evaluate whether the requested test to be performed can be performed by the analyzers in the sample processing system 100. For example, continuing with the above example, the test order may request a determination as to the presence or amount of a particular drug of abuse in a biological sample. Given this information, the control system 108 may determine that only the second analyzer 102 and the mass spectrometer 106 would have the requisite sensitivity to test for that particular drug of abuse. Thus, the desired sensitivity for the test to be performed can be compared the sensitivities of the analyzers in the parameters 112A.

In step 168, one or more analyzers are determined. The determined one or more analyzers are then used to process and analyze the biological sample. In some embodiments of the invention, the control system 108 may determine that two or more of analyzers will be used to process the biological sample. At least one of the analyzers is a mass spectrometer. The determination of which analyzers can be used to process the biological sample can depend upon a number of factors and can be based on the previously described parameters 112A and condition sets 112B. In some embodiments, the selection may specifically depend upon the accuracy of the results provided by the various analyzer types in the system, the availability of the analyzers systems, and any specific requirements of the test order for the biological sample.

In step 170, the biological sample is then processed and analyzed by one or more analyzers that were determined in step 168. Depending upon which analyzer or combination of analyzers was selected by the control system 108, any necessary sample preparation for the analyzers may take place within the sample staging apparatus 140, or it can be performed within the analyzers 101, 102, 107, or the mass spectrometer 106. The control system 108 may provide instructions to any of the determined analyzers 101, 102, 107 and/or mass spectrometer 106. In some embodiments, the control system 108 may maintain communication with the determined analyzers 101, 102, 107 and/or mass spectrometer 106 to control them during processing and analyzing the biological sample. In other embodiments, the control system 108 may provide an initiation instruction, and the analyzers 101, 102, 107 and/or mass spectrometer 106 may thereafter operate independently of the control system 108 until measurement values are produced by them.

In step 172, one or more measurement values are determined for the biological sample by the one or more analyzers. Each analyzer 101, 102, 107, or the mass spectrometer 106 may produce one or more measurement values.

In step 174, the one or more measurement values are provided from the analyzers to the information management apparatus 110, and may be stored in the data storage 110C along with other measurement values 110C-3. The measurement values may be transmitted from the analyzers to the information management apparatus 110 via the control system 108, or directly.

In step 176, after the measurement values are received by the information management apparatus 110, an output is provided from the information management apparatus 110. For example, the measurement values obtained from the biological sample may be compared to patient information 110C-1. For example, the output may relate to a report that combines the measurement values from the analyzers 101, 102, 107, and/or the mass spectrometer 106 with patient information 110C-1 such as the name of the patient or medical record number of the patient. In other embodiments, the output may be the result of a comparison of any or proposed medications of the patent to any measurement values to the measurement values. In yet other embodiments, the output might be a diagnosis or recommendation based upon the measurement values and the patient information 110C-1

In step 178, the control system 108 determines if another biological sample is to be processed. If there is, then the process continues back to step 160. If not, then the process can end.

Figure 2:
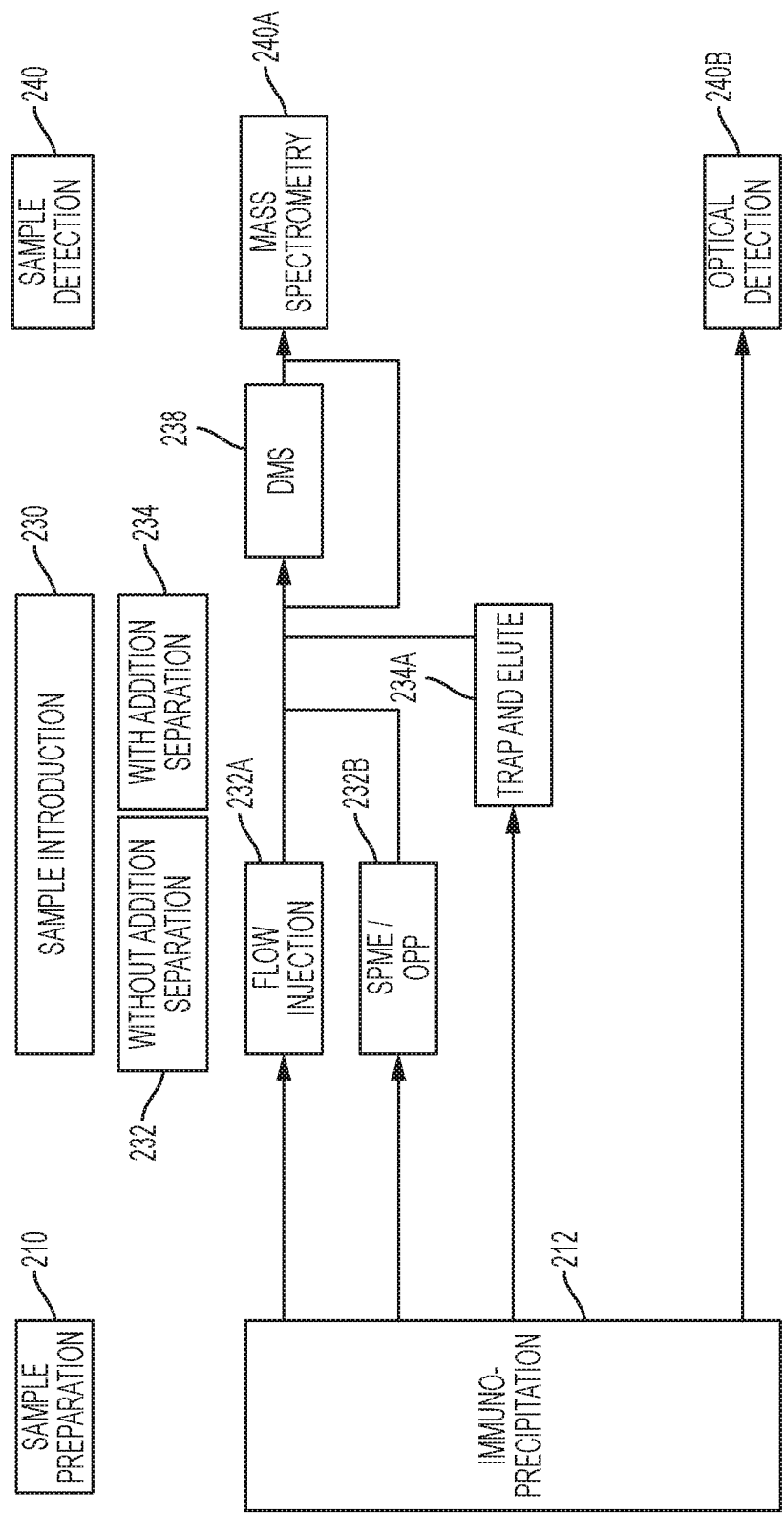
FIG. 2 shows a diagram illustrating different processing paths that can be taken in the sample processing system according to embodiments of the invention.

FIG. 2 shows a diagram illustrating different processing paths that can be taken between an analyzer such as an immunoanalyzer, and a mass spectrometer, in a sample processing system according to embodiments of the invention. A high level process flow may include a sample preparation processing module 210, a sample introduction processing module 230, and a sample detection processing module 240.

The sample preparation processing module 210 may include process steps that process a sample containing an analyte such that it may be detected during the sample detection processing module 240. In embodiments of the invention, the sample preparation processing module 210 may include an immunoprecipitation or immunopurification process. For purposes of illustration, steps in the sample preparation processing module 210 may be carried out in the second analyzer 102. Steps in the sample introduction process module may be carried out in the second analyzer 102, the mass spectrometer 106, or it may be a separate, stand-alone apparatus separate and apart from the analyzer 102 and the mass spectrometer 106. The sample detection process module 240 can be performed in the mass spectrometer 106 and/or an immunoanalyzer.

The sample introduction process module 230 includes process steps that can transfer a sample containing an analyte from the second analyzer 102 to the mass spectrometer 106. Also, the sample introduction process module 230 may include the transfer of a sample without additional separation 232 and with additional separation 234. Specific sample introduction processes that do not include additional separation 232 may include flow injection 232A or SPME (solid phase micro extraction)/OPP (open port probe) 232B. Sample introduction processes that can include additional separation can include a trap and elute process module 234A. An optional DMS (differential mobility spectrometry) process module 238 may be carried out downstream of the sample introduction process module 230 after the sample has been ionized but prior to the sample being mass analyzed.

The direct flow injection process module 232A may utilize an apparatus that can include a direct injection apparatus that can directly inject a processed sample from an analyzer into a mass spectrometer. The apparatus may include a carrier solution source, which may be used to carry the processed sample to the mass spectrometer. A pump such as a peristalic pump may be included in the direct flow injection apparatus.

The SPME/OPP process module 232B can utilize an SPME device and an OPP apparatus, which may include an open port sampling interface. SPME can integrate sampling, sample preparation, and extraction into a single solvent-free step. Generally, an SPME device utilizes a fiber or other surface (e.g., blades, micro-tips, pins, or mesh) coated with an extracting phase to which analytes within the sample can be preferentially adsorbed when the device is inserted into a sample aliquot or processed sample aliquot. An SPME device can be proximate to an OPP, which can be a vertically aligned, co-axial tube arrangement enabling solvent delivery to a sampling end (open-port) through the tubing annulus and aspiration down the center tube into an ion source driven by a nebulizer gas.

Figure 7A:
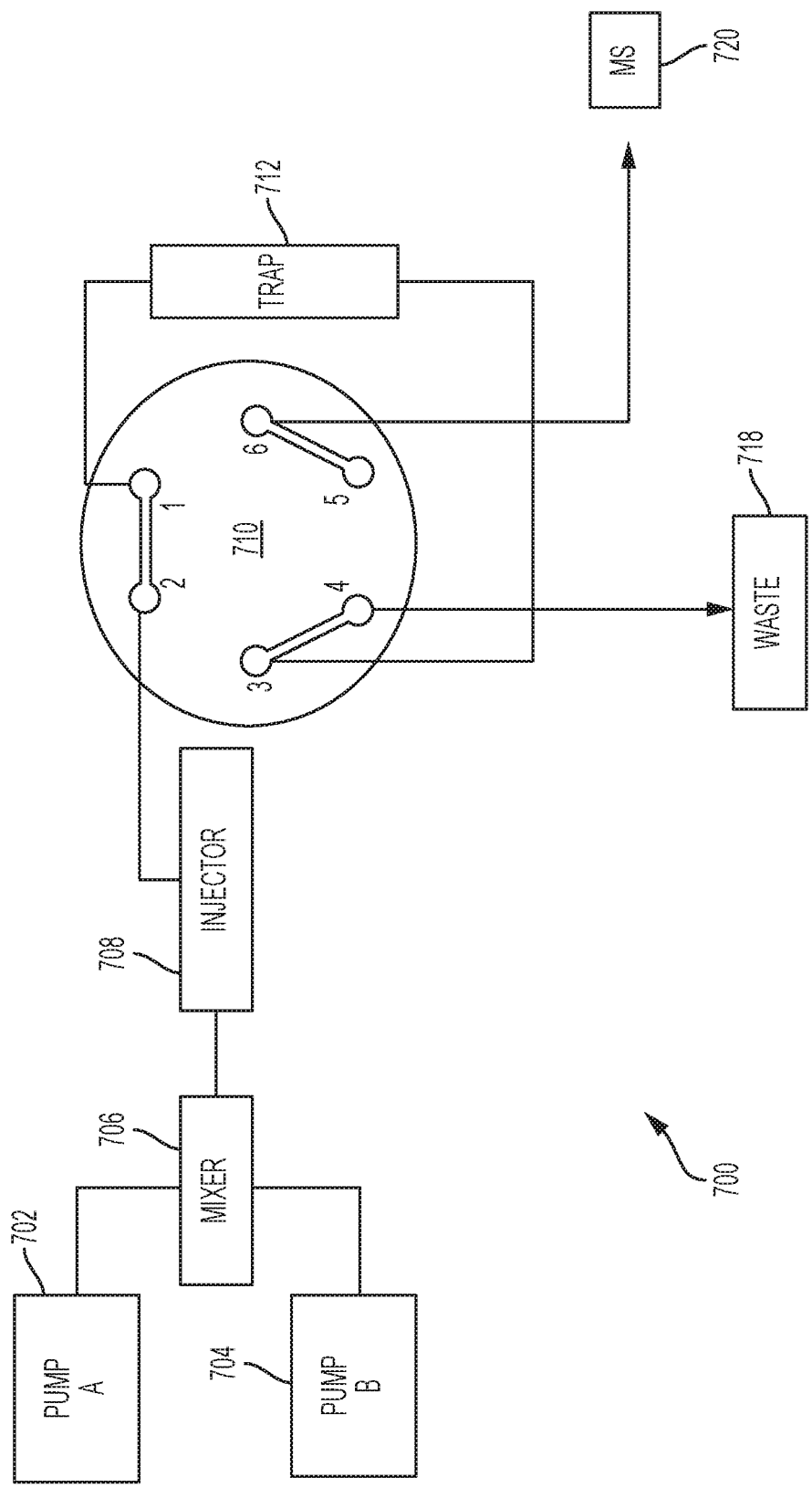
FIG. 7A shows a diagram of trap and elute system according to an embodiment of the invention in a first configuration.
Figure 7B:
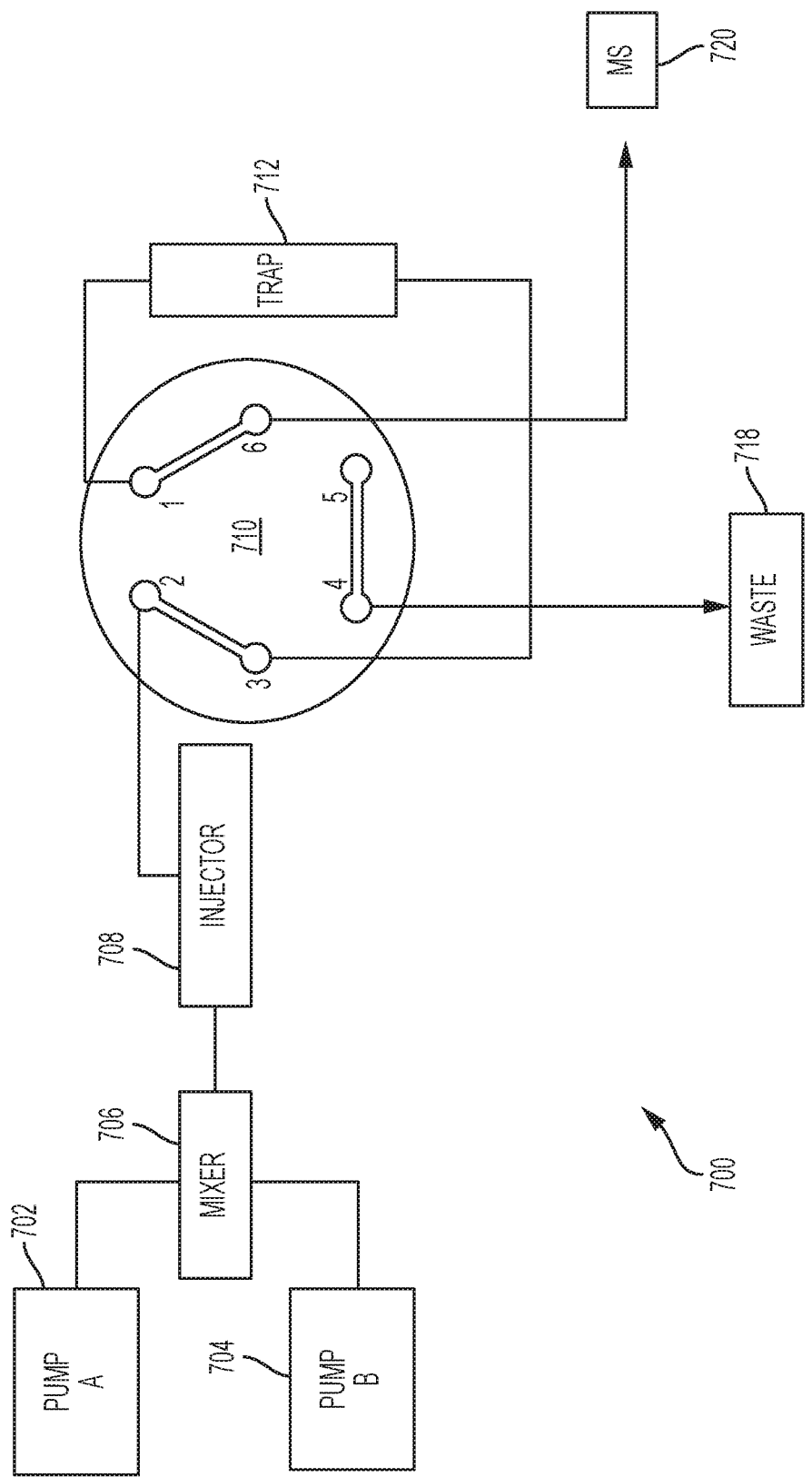
FIG. 7B shows a diagram of trap and elute system according to an embodiment of the invention in a second configuration.

The trap and elute process module 234A may utilize a trap and elute apparatus. The trap and elute process module 234A can involve injecting a sample into a small-volume column where analytes of interest are concentrated before elution into the mass spectrometer. The trapping process optimizes sensitivity and selectivity, and improves robustness. Schematic diagrams of exemplary trap and elute apparatuses are shown in FIGS. 7A and 7B, which are described in further detail below.

In other embodiments, instead of a trap and elute process module, a hydrocarbon (e.g., C18) coated tip can be used. Such tips are commercially available.

The sample introduction process module 230 could also include mechanical reaction vessel transport devices. Such transport devices may include pick and place apparatuses such as pick and place transfer gantrys, transfer shuttles such as extended linear reaction shuttles, or combinations of the pick and place transfer gantrys and extended linear reaction shuttles.

The sample detection process module 240 may include steps that are used to detect the presence, absence, and/or quantity of a particular analyte in a sample. The sample detection process module 240 may include the use of a mass spectrometric process module 240A and/or an optical detection process module 240B. The optical detection process module 240B may use a chemiluminescence or fluorescence based detection process. Other details regarding the mass spectrometric process module 240A and the optical detection process module 240B are provided below.

Figure 3:
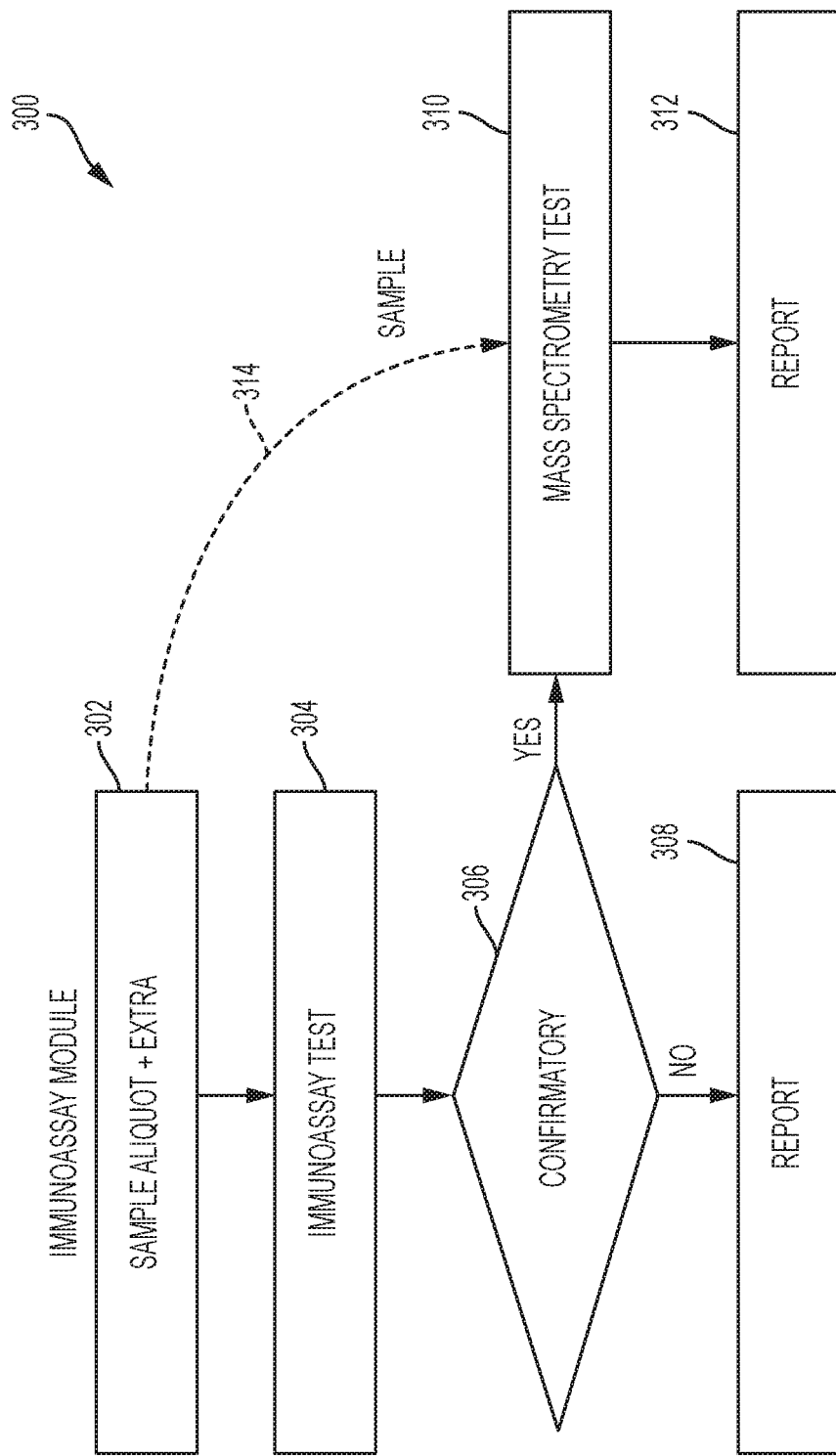
FIG. 3 shows a high level flowchart illustrating processing steps performed by a sample processing system according to embodiments of the invention. The flowchart illustrates different detection operations that can be performed in the sample processing system.

FIG. 3 shows a high level flowchart 300 illustrating the different types of detection processes that can be performed using the sample processing system according to embodiments of the invention. In the flowchart 300, the ability to detect the presence, absence, and/or concentration of a particular analyte using an optical detection process and a mass spectrometric process is shown. It is apparent that embodiments of the invention have a great deal of flexibility in determining if an analyte is or is not present in a particular sample.

In step 302, an analyzer can obtain two or more or more sample aliquots of a sample and can dispense them into two or more reaction vessels. If the analyzer is an immunoanalyzer, one of the sample aliquots may be subjected to an immunoassay test in the immunoanalyzer at step 304. A first reaction vessel including a first sample aliquot may be processed by the immunoanalyzer to form a first processed sample aliquot. Then, the immunoanalyzer may be used to detect if a particular analyte is present or absent in the first processed sample aliquot in the reaction vessel.

After the immunoassay test is performed on the first processed sample aliquot, the control system in the sample processing system can make a decision as to whether a confirmatory test is desired in step 306. If a confirmatory test is desired, the second sample aliquote in the the second reaction vessel can be processed by the analyzer to form a second processed sample aliquot. The second processed sample aliquot may be transferred from the analyzer to a mass spectrometer in step 314. Once the processed second aliquot is in the mass spectrometer, the mass spectrometer may perform a mass analysis on the processed second aliquot in step 310. After the mass analysis is performed on the processed second aliquot, a report may be generated in step 312. If a confirmatory test is not desired, then a report may be generated in step 308 without performing a mass spectrometric analysis in step 310.

In some embodiments, data from the immunoanalyzer may indicate that the concentration of the analyte in the first processed sample aliquot is below, above or equal to a predetermined threshold in a primary analysis. The control system may then have determined that a reflex process on the sample may be desirable or necessary. The method may then further include causing the analyzer to process a second aliquot of the sample to form the second processed sample aliquot. The sample introduction apparatus may transfer the second processed sample aliquot from the analyzer to the mass spectrometer. The control system may then cause the mass spectrometer to detect the presence of one or more other analytes in the second processed sample aliquot in a secondary analysis.

In some cases, the detection of the analyte in the primary analysis may indicate that a particular condition (e.g., a medical condition) may be present. However, to confirm that the particular condition is present, the secondary analysis may analyze for a second analyte using mass spectrometry. Together, the presence or absence of the first and second analytes may indicate that the presence of the particular condition is present.

The above described threshold may be any suitable value. For example, the threshold may be that a predetermined quantity (e.g., amount) or concentration of a particular analyte(s) needs to be present in a processed sample aliquot before it can be concluded with a degree of confidence that the analyte is or is not present in the processed sample aliquot.

The use of the mass spectrometric analysis in a reflex process is desirable. In some instances, when a sample is tested for an analyte in a traditional immunoanalyzer, non-specific binding can occur on the antibodies and/or the magnetic beads to which they are attached. This may affect the accuracy of the analysis being conducted. Mass spectrometric analyses are not subject to the problems associated with non-specific binding, and can thus serve as an effective mechanism for reflex testing, or testing in general.

Figure 4A:
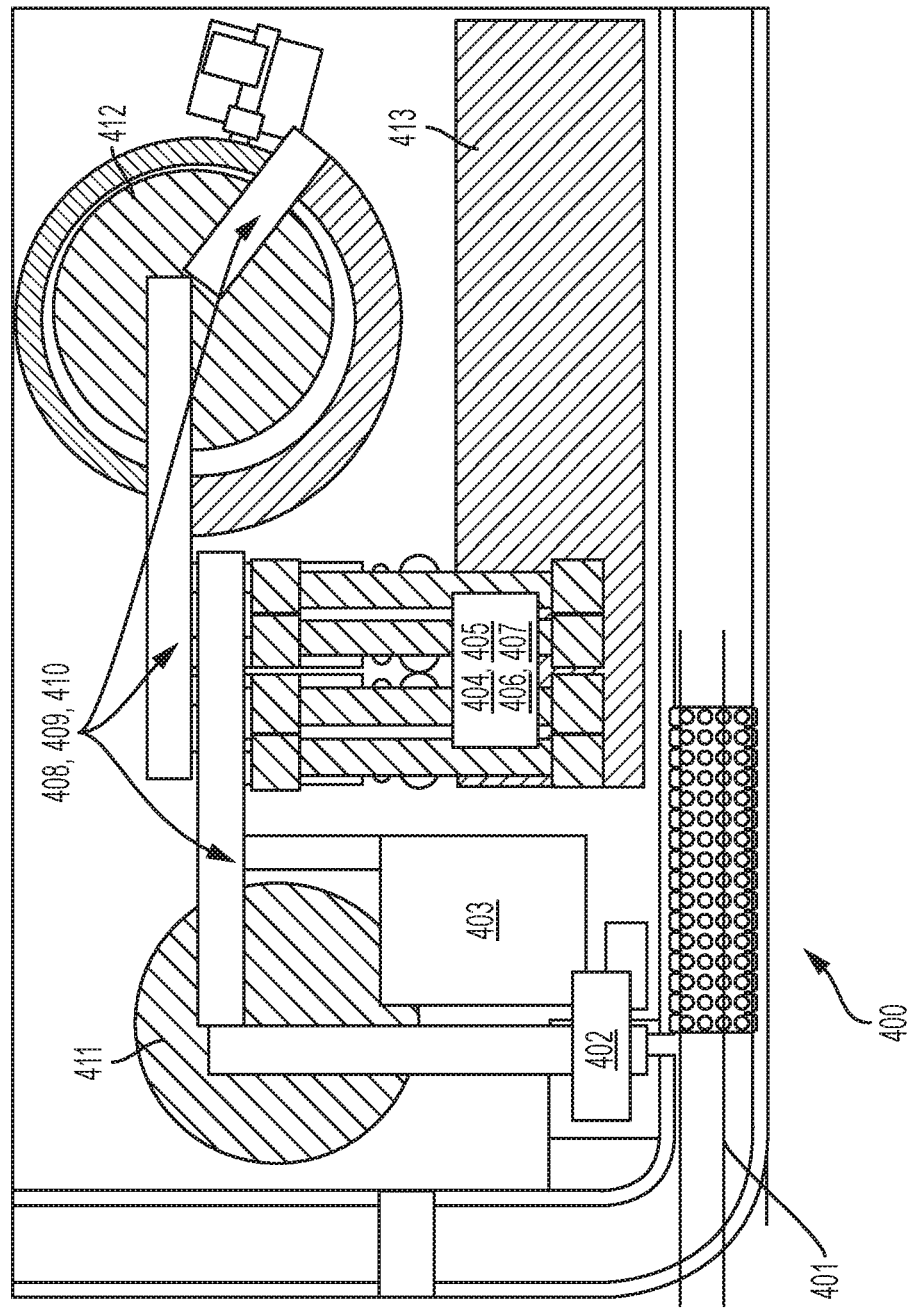
FIG. 4A shows a diagram of an analyzer in a sample processing system according to an embodiment of the invention.

FIG. 4A shows a block diagram of an automated immunochemistry analyzer 400 that can be used in an automated sample processing system according to an embodiment of the invention. The basic structural and functional modules of the automated immunochemistry analyzer 400 can include a sample presentation unit 401, a main sample pipetting station 402, a bulk vessel feeder 403, first dual reagent pipetting stations 404 and 405, second dual reagent pipetting stations 406 and 407, a first pick-and-place gripper 408, a second pick-and-place gripper 409, a third pick-and-place gripper 410, an incubator/wash/read station 412, a sample storage 411, and a reagent storage 413. Optionally, the sample and/or reagent storage can be chilled.

The sample presentation unit 401 can used to transport an entire required test sample to and from the main sample pipetting station 402. A detailed description of the configurations and functions of the sample presentation unit 401 is provided in U.S. Pat. No. 6,790,413, filed on May 3, 2001, which is incorporated herein by reference in its entirety.

The main sample pipetting station 402 can be used to aspirate samples out of the sample tubes and dispense them into reaction vessels supplied by the bulk vessel feeder 403. A detailed description of the configurations and functions of the bulk vessel feeder 403 is provided in U.S. Pat. No. 6,790,412, filed on Feb. 6, 2001, which is incorporated herein by reference in its entirety.

The four reagent pipetting stations 404, 405, 406, and 407 can be used to mix a sample with reagents for subsequent assays. The four reagent pipetting stations 404, 405, 406, and 407 can be arranged as two dual pipetting stations and can be independent to each other. Each of the four reagent pipetting stations 404, 405, 406, and 407 can have its own fluid pumps and valves, wash towers, reaction vessel carriages, and pipettor(s). Although four pipetting stations 404, 406, 406, 407 are illustrated, it is understood that embodiments of the invention can include more or less of the pipetting stations.

The three vessel pick-and-place grippers 408, 409, 410 can be used to transport sample and reaction vessels among the various modules of the analyzer. The first pick-and-place gripper 408 can be used to transport reaction vessels between the bulk vessel feeder 403 or the sample storage 411 and the reagent pipetting stations 404, 405, 406, 407. The second pick-and-place gripper 409 can be used to transport reaction vessels between the reagent pipetting stations 404, 405, 406, 407 and the incubator of the incubator/wash/read station 412. The third pick-and-place gripper 410 is used to transport reaction vessels between the incubator and the wash wheel (an example of a wash station) of the incubator/wash/read station 412. A detailed description of the configurations and functions of the vessel pick-and-place grippers 408, 409, and 410 is provided in U.S. Pat. No. 7,128,874, which is herein incorporated by reference in its entirety. It is understood that embodiments of the invention can have more or less pick-and-place grippers.

The sample storage 411 can be used for storing the samples contained in the reaction vessels at a low temperature for a certain period of time, e.g., up to three (3) hours, so that the samples may be used for retesting or reflex testing. When a test is requested on a patient sample, the test outcome may drive a request for additional testing. As noted above, this automatic request for additional tests is reflex testing. The time delay from the first aspiration to knowing if another test will be started can range to as long as 45 minutes or more. To hold a sample tube for such a period of time prevents the sample from being used in other places. If the tube is passed to other instruments, it may be difficult for a laboratory technician to find the tube and reload it on the instrument requesting the reflex test. To allow a single quick sample draw on sample tubes that might require reflex testing, a single aspiration (aliquot) can be taken with sufficient test material for the possible reflex test(s). However, to insure that the test materials do not evaporate or deteriorate, the aliquot may need to be refrigerated on board the analyzer.

The sample storage 411 can one or more reaction vessels containing sample aliquots for samples that are being processed in primary analyses. The sample aliquots stored in the sample storage 411 can be used to perform secondary analyses (e.g., reflex tests) on either the analyzer or the mass spectrometer.

Figure 4B:
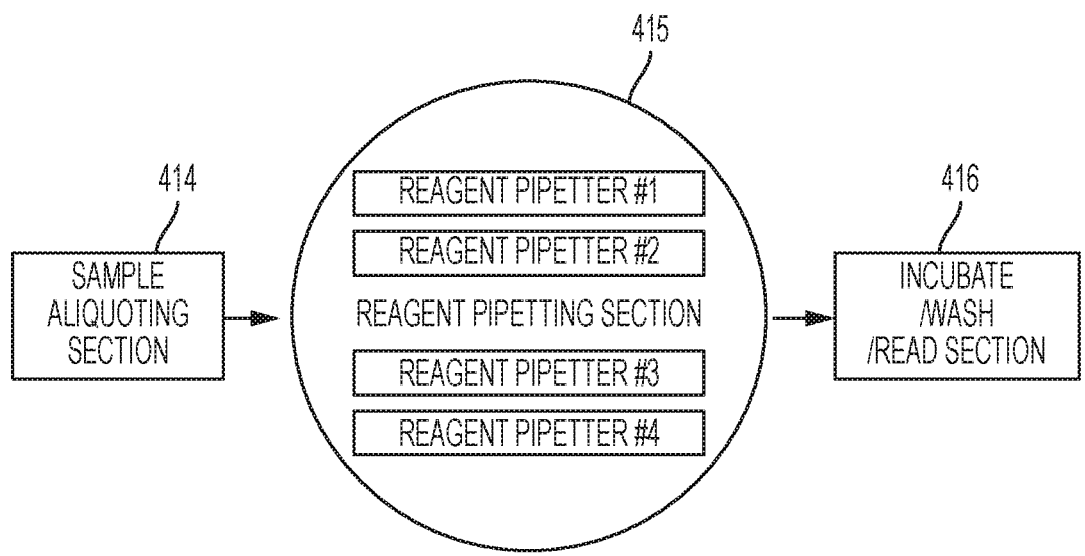
FIG. 4B shows an illustrative flow chart diagram showing operating procedures for operating an analyzer.
Figure 4C:
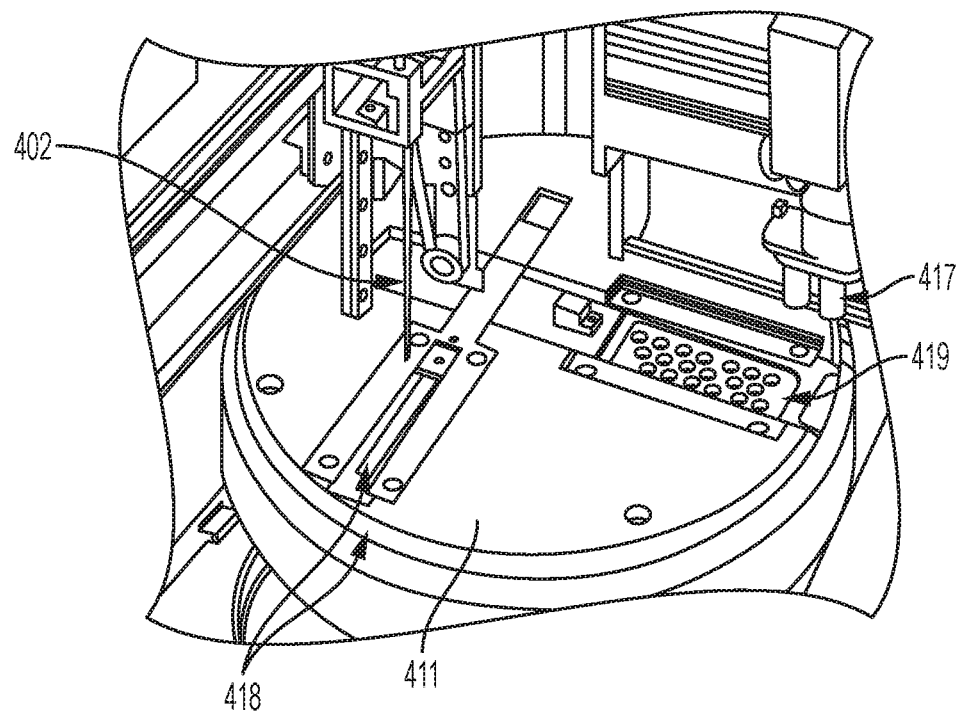
FIG. 4C shows a perspective view showing an arrangement of a main sample pipetting station and a sample storage of the analyzer.

Referring to FIG. 4C, there is shown the arrangement of the main sample pipetting station 402 and the sample storage 411 of the automated immunochemistry analyzer. The pipettor of the main sample pipetting station 402 first aspirates samples from sample tubes, and then moves into a position above the sample storage 411. Meanwhile, the sample storage 411 first receives an empty reaction vessel from the bulk vessel feeder 403 by the pick and place gripper 417, and then moves the empty reaction vessel under the pipettor of the main sample pipetting station 402. The aspirated sample is then dispensed into the chilled reaction vessel. Insulation and doors 418 are provided to control the environment in the sample storage 411. The sample storage 411 can be a precision controlled refrigerator with multiple storage locations 419 capable of receiving and transferring reaction vessels for or filled with sample material. Sample aliquots can be present in reaction vessels that are stored in the sample storage 411. These samples can be used for retesting or reflex testing in the immunoanalyzer or in the mass spectrometer.

The incubator/wash/read station 412 can be used for the incubating, washing, and reading steps of the assays. In some embodiments, the incubator/wash/read station 412 may be generically characterized as a separation station. It may include one or more incubators, one or more assay wash stations, and one or more readers, such as a photomultiplier tube (PMT) detector, or other optical detection systems. A detailed description of the configurations and functions of the incubator/wash/read station is provided in U.S. Pat. No. 7,217,391, filed on Mar. 16, 2001, which is herein incorporated by reference in its entirety.

As a way of minimizing background signals from excess or unbound materials, immunoassays generally use one or more separation phases be carried out in the reaction vessel. To facilitate the separation or washing process, a variety of techniques can be used, including, but not limited to, well coating techniques, bead coating techniques, or the use of paramagnetic particles. Each of these separation media are coated with a capture reagent (e.g., antibody) that will bind analyte molecules of interest in a sample. When paramagnetic particles are used as the separation media, the paramagnetic particles are pulled to the wall of the reaction vessel by magnets during the washing process and the supernatant is aspirated. Luminescent labels are then bound to these analyte molecules. When a luminescing reagent or substrate is added to the reaction vessel, it reacts with the luminescent label to produce light that is detectable by the analyzer's optical detection station.

The reagent storage 413 can be used for storing reagents used for the immunoassays as well as the mass spectrometric process. The reagent packs may include reagents that are in liquid or solid form. The reagent storage 413 can store reagent packs in a refrigerated environment until requested for use, transfer a pack to an appropriate reagent pipetting station when requested for use, and return the pack to storage when pipetting is complete. It can also return a full or partially used pack to the operator when requested and automatically dispose of empty packs. The temperature in the reagent storage 413 can be controlled by Peltier devices and monitored with a thermistor.

For immunoassays, some types of reagents can include paramagnetic particles with or without coating of antibodies or antigens, blocking agents, antibodies, assay buffers, antibodies conjugated to enzymes (for chemiluminescence), sample pre-treatment reagents such as acids, bases, or releasing agents.

For mass spectrometry, mass spectrometric reagents such as mass tags (e.g., Amplifex™ mass tags) can be used during the sample preparation process to enhance signals and improve sensitivity. As noted above, reagents such as this can be used with the second sample aliquot that will be processed for a mass spectrometric analysis.

The reagent packs can be loaded into the reagent storage 413 as follows: (a) an input tray cover is opened by the operator and the input tray is positioned, if necessary, to allow the operator to place reagent packs into the tray; (b) the input tray cover is closed and the input tray closes, bringing the reagent packs into the reagent storage 413; (c) as the input tray closes, each reagent pack position passes a bar code reader (BCR), where each of the four pack positions is read and identified; (d) a reagent pack gripper of a reagent pack transporting and sorting mechanism moves to get a pack from the input tray that was identified by the bar code reader; (e) the reagent pack gripper of the reagent pack transporting-and-sorting mechanism moves the reagent pack to either a storage location or a pipetting location (if needed), and drops the reagent pack off, and (f) the above steps (d) through (e) can be repeated, until all reagent packs are removed from the input tray.

The reagent storage 413 includes a mechanism for transporting and sorting multiple reagent packs. A detailed description of the configuration and functions of such a mechanism for transporting and sorting multiple reagent packs is provided in U.S. Pat. No. 6,746,648, filed on Jun. 15, 2000. Other structures and functions of the reagent storage 413 conform to existing arrangements known to those of ordinary skill in the art, and therefore will not be described in detail here.

FIG. 4B shows an illustrative flow chart diagram showing the basic operating procedures of the method of automated immunochemistry analysis.

The basic operating procedures of the automated immunochemistry analysis can be carried out in three main sections of the automated immunochemistry analyzer: a sample aliquoting section 414, where the sample is aspirated out of a sample tube and dispensed into a reaction vessel, a reagent pipetting section 415, where the sample is mixed with reagents, and an incubate/wash/read section 416, where the mixed sample is incubated, washed, and separated from particulates and read by the photo-multiplier tube (PMT) detector or other optical detection station.

The sample aliquoting section 414 and the incubate/wash/read section 416 each has one set of units, and works on a cycle (in one embodiment, a nine (9)-second cycle). The reagent pipetting section 415 can have four (4) independently working reagent pipetting stations, where each reagent pipetting station works on second cycle (in one embodiment, a thirty-six (36) second cycle).

However, the scheduling of the four reagent pipetting stations can be staggered (in one example, nine (9) seconds apart). For example, the analyzer can accept one (1) test sample in every nine (9) seconds, i.e., the analyzer has an effective cycle of nine (9) seconds. Accordingly, the analyzer can have a fast throughput (e.g. four hundred (400) tests per hour). Embodiments of the invention are not limited to these timings or values.

Referring to FIGS. 4A and 4B, the basic operating procedures of the sample aliquoting section 414, the reagent pipetting section 415, and the incubate/wash/read section 416 and are described below:

A. The Operating Cycle of the Sample Aliquoting Section 414

1. The user loads a sample rack containing up to four (4) sample tubes on the sample presentation unit 401.

2. The rack is advanced into the main sample pipetting station 402 where the sample may be identified by a bar code reader (BCR) and presented to the main sample pipetting station 402.

3. At the same time, the bulk vessel feeder 403 presents the reaction vessel necessary for the tests to a sample reaction vessel carriage, from where the first pick-and-place gripper 408 picks the reaction vessel up and stores it in the sample storage 411 and/or in the reaction vessel carriage of any one of the available reagent pipetting stations 404, 405, 406, 407.

4. The main sample pipetting station 402 aspirates the amount of sample required and aliquots it into the reaction vessel in the sample storage 411, and afterwards, the probe is washed in its dedicated wash station. The sample probe can be washed to reduce sample carry-over to a level that will not adversely affect other samples.

B. The Operating Cycle of the Reagent Pipetting Section 415

1. The first pick-and-place gripper 408 picks up the reaction vessel containing the aliquoted sample and moves it over to an available reagent pipetting station.

The following describes this process: (a) a requested reaction vessel in the sample storage 411 is positioned under an operating position of the first pick-and-place gripper 408; (b) a reaction vessel carriage of an available reagent pipetting station is positioned under another operating position of the first pick-and-place gripper 408; and (c) the first pick-and-place gripper 408 transfers the requested reaction vessel from the sample storage 411 to the reaction vessel carriage of the available reagent pipetting station.

2. At the same time, the reagent storage 413 brings a required reagent pack to the same reagent pipetting station.

3. With the reagent pack and reaction vessel in position, the reagent pipettor of that reagent pipetting station aspirates a required amount of sample from the sample reaction vessel and dispenses it into an assay reaction vessel and also retrieves a required amount of reagent from the reagent pack and dispenses it into the assay reaction vessel, and afterwards, the probe is washed in its dedicated wash station.

The following describes the process of sample aspiration: (a) the reagent pipettor of the reagent pipetting station is positioned over the reaction vessel; (b) an ultrasonic level sense circuit is used to detect the surface of the sample, and lowering of the pipettor is halted once the surface is found and the pipettor is just deep enough to draw the needed sample volume (therefore reducing carry-over); and (c) the sample is drawn up using the precision pump and valve, where an in-line pressure profile is collected by using a pressure sensor during the sample aspiration, which profile can be used to verify proper sample pickup. A detailed description of the configurations and functions of a precision pump and valve that are used herein are provided in U.S. Pat. Nos. 6,520,755 and 6,843,481, which are herein incorporated by reference in their entirety.

The following describes the process of reagent aspiration: (a) the reagent pipettor of the reagent pipetting station moves to the appropriate reagent well location of the reagent pack; (b) the reagent pipettor is lowered into the reagent pack well, and if this is a particle well, then an ultrasonic mix circuit is enabled (and the lock signal is checked to ensure proper operation) to mix the particles prior to aspiration; and (c) the reagent is drawn up using the precision pump and valve, where an in-line pressure profile is collected by using a pressure sensor during the reagent aspiration, which profile is used to verify proper reagent pickup.

The following describes the process of a sample or reagent delivery: (a) the reagent pipettor of the reagent pipetting station moves to the assay reaction vessel location in the reaction vessel carriage of the pipetting station; (b) the reagent pipettor is lowered into the assay reaction vessel, where the exact dispense height is calculated to have the sample or reagent just touch the probe after it has been dispensed (to ensure that there is no sample or reagent drop left on the tip of the probe); and (c) the sample or reagent is dispensed using the precision piston pump and valve, where an in-line pressure profile is collected by using a pressure sensor during the sample delivery, which profile is used to verify proper sample or reagent delivery.

The following describes the process of sample dilution: (a) the appropriate sample reaction vessel is retrieved for pipetting; (b) the dilution location in a reagent vessel carriage of an available reagent pipetting station is positioned under the operating position of the first pick-and-place gripper 408; (c) the bulk vessel feeder supplies two empty vessels (the reaction vessel and the dilution vessel); (d) the first pick-and-place gripper 408 transfers both vessels simultaneously to the reagent vessel carriage of the available reagent pipetting station; (e) the sample is aspirated and delivered to the dilution vessel along with an additional volume of buffer using the precision piston pump and valve, where the exact dispense height is calculated to have the diluted sample just touch the probe after it has been dispensed (to ensure that there is no sample drop left on the tip of the probe) or to go slightly deeper if mixing is requested (in such case, the ultrasonic mix circuit is enabled and the lock signal is checked to ensure proper operation); (f) a specific volume of this diluted sample is aspirated using the precision pump and valve, where an in-line pressure profile is collected by using a pressure sensor during the aspiration, which profile is used to verify proper diluted sample pickup; (g) the original reaction vessel is returned to the sample storage 411 if there is sample left or is disposed of if it is empty; and (h) the vessel containing the diluted sample now becomes the reaction vessel for the subsequent assay being processed.

The following describes the process of sample and reagent addition: (a) the requested sample is retrieved from the sample storage 411; (b) the bulk vessel feeder supplies an empty reaction vessel to the vessel supply carriage; (c) the vessel supply carriage is positioned under the operating position of the first pick-and-place gripper 408; (d) the reagent vessel carriage of an available reagent pipetting station is positioned under the other operating position of the first pick-and-place gripper 408; (e) the first pick-and-place gripper 408 transfers the empty reaction vessel to the reagent vessel carriage of the available reagent pipetting station; (f) the reagent vessel carriage is positioned for pipetting; (g) the requested reagent pack is also positioned for pipetting; (h) the reagent pipettor of the reagent pipetting station moves to a reagent wash tower, then down into the reagent wash tower, for washing the probe; (i) the sample is aspirated and delivered to the reaction vessel; (j) the reagent pipettor moves to the reagent wash tower, then down into the reagent wash tower, for washing the probe; (k) the reagent pipettor aspirates the appropriate amount of reagent and delivers it to the reaction vessel; (l) the above steps (j) and (k) are repeated until all of the reagents have been delivered to the reaction vessel; (m) if reaction vessel mixing is desired, the probe moves down slightly and the ultrasonic mix circuit is enabled and the lock signal is checked to ensure the proper operation; (n) the reagent vessel carriage is positioned under an operating position of the second pick-and-place gripper 409; (o) an empty position on a reaction vessel incubator wheel is positioned under another operating position of the second pick-and-place gripper 409; (p) the second pick-and-place gripper 409 transfers the reaction vessel into the incubator of the incubating/wash/read station 412; (q) in the case of two or three step assays, the second pick-and-place gripper 409 will bring the reaction vessel back to a pipetting location and additional reagents will be added, and then the vessel is transferred back to the incubator of the incubating/wash/read station 412 by the second pick-and-place gripper 409 for the second or third incubation.

The reagent probe can be washed to reduce sample and reagent carry-over to a level that will not adversely affect other samples or reagent. The following describes this process: (a) the ultrasonic circuit is enabled to wash the reagent probe; (b) a vacuum pump evacuates the tower, while the tower's evacuation line pressure is monitored to ensure that the tower is draining properly; (c) the probe is flushed internally with buffer using the precision pump and precision valve and showered externally using the peristaltic pump; and (d) the buffer flow is stopped while the vacuum pump and ultrasonic circuit run slightly longer to ensure that the probe is dried.

4. The second pick-and-place gripper 409 picks up the assay reaction vessel containing the mixture of sample and reagent and moves it over to an incubator wheel of the incubator/wash/read station 412.

5. The first pick-and-place gripper 408 picks up the sample reaction vessel containing the remaining aliquoted sample and returns it to the sample storage 411 if reflex testing is required or else ejects it to a waste container.

The following describes this process: (a) a sample storage location in the sample storage 411 is positioned under the operating position of the first pick-and-place gripper 408; (b) the reaction vessel carriage of the reagent pipetting station is positioned under the other operating position of the first pick-and-place gripper 408; and (c) the first pick-and-place gripper 408 transfers the sample reaction vessel from the reaction vessel carriage of the available reagent pipetting station to the sample storage 411.

C. The Operating Cycle of the Incubate/Wash/Read Section 416

1. The assay vessel remains in the incubator wheel for a programmed time at a controlled temperature with heater elements and is monitored with a thermistor, and then picked up by the third pick-and-place gripper 410 for washing.

2. The wash/read ring has multiple aspirate stations and multiple dispense stations and the assay reaction vessel goes through several operations, including particle washing, substrate addition and incubation, etc., under a controlled temperature with heater elements and monitored with a thermistor.

3. The assay reaction vessel is read by the reader/detector, and thereafter is put back to the incubator by the third pick-and-place gripper 410, and thereafter picked up and disposed in the waste container by the second pick-and-place gripper 409.

The operations of the analyzer are supported by fluid systems, electronic control hardware; and software, including various sensors and micro-controller(s), electrical power supply units, motors, and driving mechanisms, and mechanical structures, and the determination of suitable materials and structures are within the skill in the art.

The method performed in an automated immunochemistry analysis can also include the following steps: (a) adjusting the respective cycle of at least one of the at least two procedures, such that one of the least two procedures has an operating cycle of a first period of time and another one of the at least two procedures has an operating cycle of a second period of time, and the quotient of the second period of time divided by the first period of time is a whole number; (b) providing a plurality of independent working stations for performing the other one of the at least two procedures, each working station operating on the cycle of the second period of time, such that the number of such stations equal to the whole number; and (c) staggering apart respective cycles of the independent working stations by the first period of time, such that at least one of the working stations is available for each operating cycle of the first period of time.

The analyzer has many unique features and advantages. First, the analyzer can be capable of having a high throughput, e.g., 400 tests per hour. Second, the analyzer can be capable of providing multiple pipetting modules that can work independently to ensure uninterrupted analysis, even when one of the modules malfunctions. Third, the analyzer can perform retesting or reflex testing with a large capacity sample storage area.

Figure 5A:
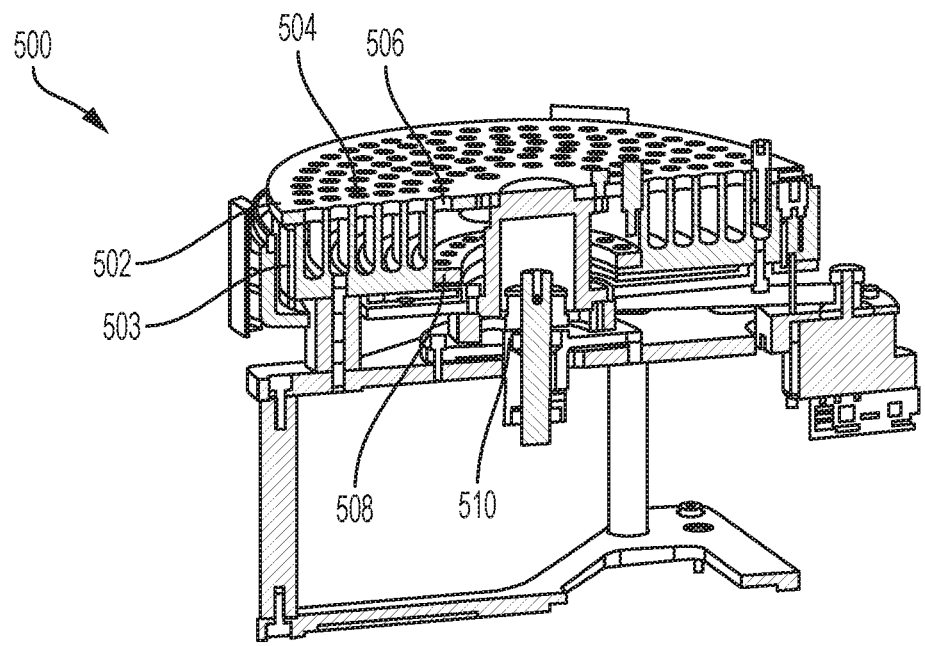
FIG. 5A shows a top/side cross-sectional view of an incubation carousel according to an embodiment of the invention.
Figure 5B:
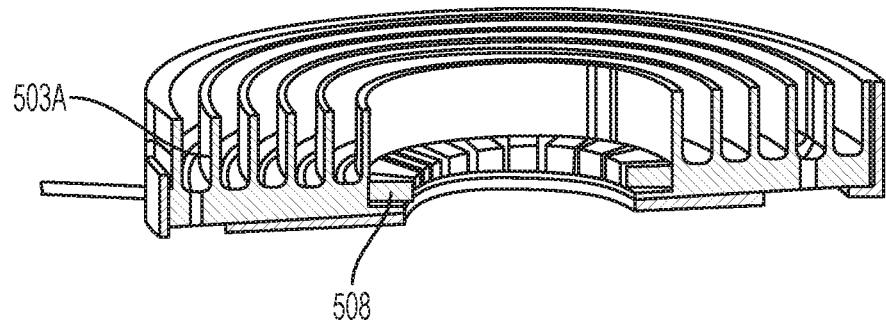
FIG. 5B shows a top/side perspective and cross-sectional view of a portion of the incubation carousel in FIG. 5A.
Figure 5C:
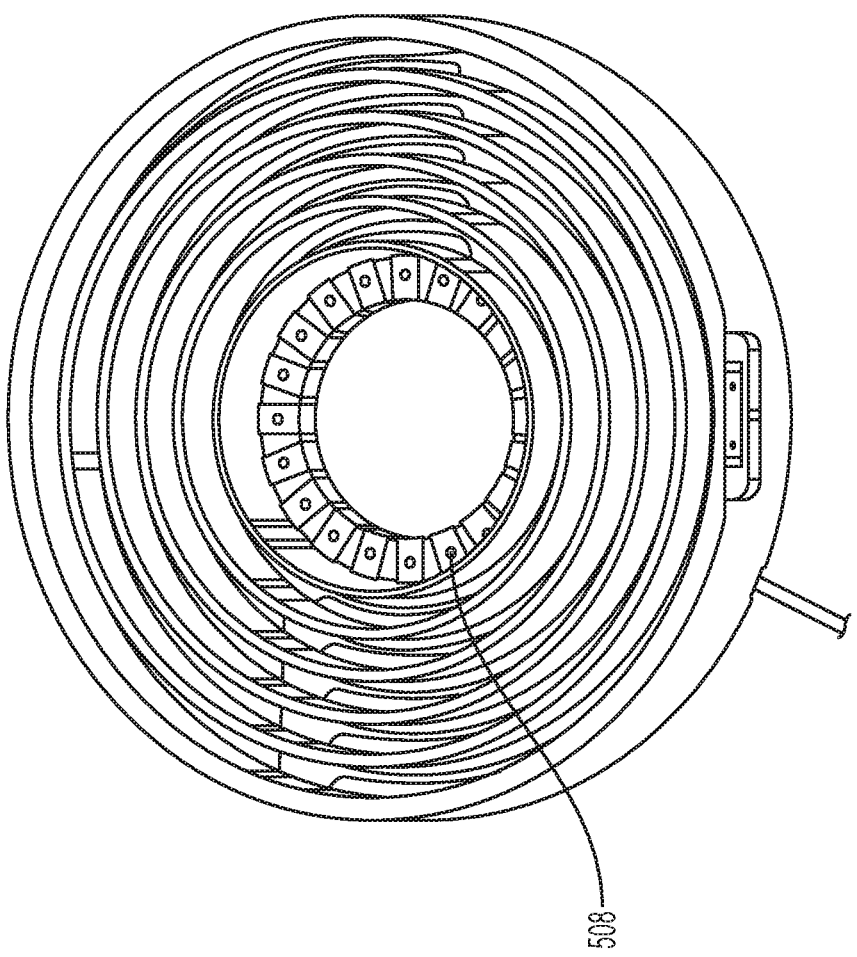
FIG. 5C shows a top perspective view of a portion of the incubation carousel in FIG. 5A.

FIG. 5A shows a cross-sectional view of an incubation carousel 500 according to an embodiment of the invention. FIG. 5B shows a cross-section of a portion of the incubation carousel 500. FIG. 5C shows a top perspective view of a portion of the incubation carousel 500.

Referring to FIG. 5A, the incubation carousel 500 can include a body including a top portion 502 in the form of a circular plate with an array of holes 504 for receiving reaction vessels with samples to be processed. Each hole 504 may correspond to a discrete incubation region where a reaction vessel may be subjected to an incubation process. The top portion 502 sits on top of a bottom portion 503, which includes a number of concentric walls 503A (shown in FIG. 5B). The body is situated on an axis 510 that can cause the incubation carousel 500 to rotate. If desired, heaters such as thin film heating elements may be included within the body so that samples within the holes 504 can be heated if desired. The incubator carousel 500 can have other shapes, or more or less holes than are specifically illustrated.

Magnets 508 can be present within the bottom portion 503 of the body of the incubation carousel. 500. As shown in FIGS. 5A-5C, the magnets 508 are present in the innermost circle of incubation regions, but they part of any suitable number of incubation regions. The magnets may used to bind magnetic particles so that any supernatant that is suitable for a downstream mass spectrometric analysis can be performed. The magnets may be permanent magnets or electromagnets. An aspiration device (not shown) such as a pipettor may remove any supernatant and may transfer the supernatant to a sample introduction apparatus, for eventual transfer to the mass spectrometer.

A wide variety of mass analyzer systems, which can form part of the mass spectrometers, can be used in the sample processing system according to embodiments of the invention. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, by interaction with an electron beam (e.g., electron induced dissociation (EID), electron capture dissociation (ECD)), interaction with thermal radiation (e.g., thermal/black body infrared radiative dissociation (BIRD)), post source decay, or combinations thereof.

Examples of suitable mass spectrometers include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

In various embodiments, the mass spectrometer comprises a MALDI ion source. In various embodiments, at least a portion of the combined sample is mixed with a MALDI matrix material and subjected to parent-daughter ion transition monitoring using a mass analyzer with a MALDI ionization source.

The mass spectrometer can comprise a triple quadrupole mass spectrometer for selecting a parent ion and detecting fragment daughter ions thereof. In this embodiment, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

One or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

In some embodiments, the mass spectrometer can comprise two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

In some embodiments, the mass spectrometer can comprise two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

The mass spectrometer can comprise a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In some embodiments, ionization can be used to produce structurally specific fragment ions and Q3 MRM ions. A labeling reagent can be wholly or partly contained in the structurally specific fragment ions. The method can provide both sensitivity and specificity for the Q3 MRM ions. In some embodiments, ionization can be used to produce a dominant neutral loss fragment ion which can be selected in Q3 and then fragmented to produce structurally specific ions. These fragment ions can then be used for identification and quantification in a procedure referred to as MS3.

Figure 6A:
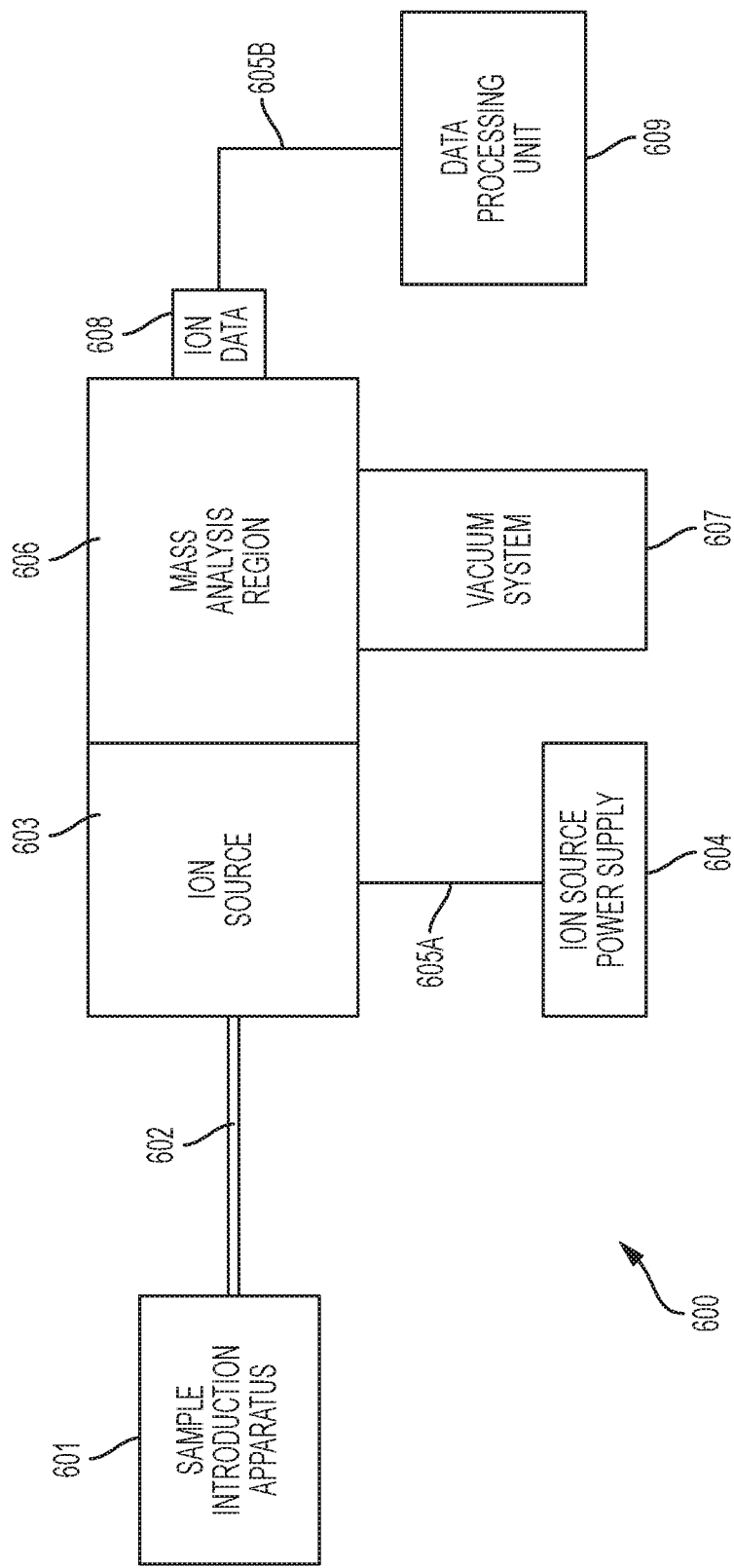
FIG. 6A shows a block diagram of a mass spectrometer.

FIG. 6A shows a block diagram of an exemplary mass spectrometer 600 and a sample introduction apparatus 601 coupled to the mass spectrometer. A sample solution may have been transferred from the analyzer, into the sample introduction apparatus 601. The sample introduction apparatus 601 can be in the analyzer in some embodiments. The sample introduction apparatus 601 may be coupled to the mass spectrometer 600 through a connecting tube 602. The sample introduction apparatus 601 may introduce the sample solution to the ion source 603 through the connecting tube 602. The ion source 603 can be controlled by an ion source power supply 604 through a signal line 605A. Ions concerning sample molecules, which are generated by the ion source 603, are introduced to a mass analysis region 606 and mass analyzed. The mass analysis region 606 is evacuated to a vacuum by a vacuum system 607. The ions thus mass analyzed are detected by an ion detector 608. A detection signal is fed through a signal line 605B to a data processing unit 609. The data processing unit 609 may be a separate unit or may be part of the previously described control system.

Figure 6B:
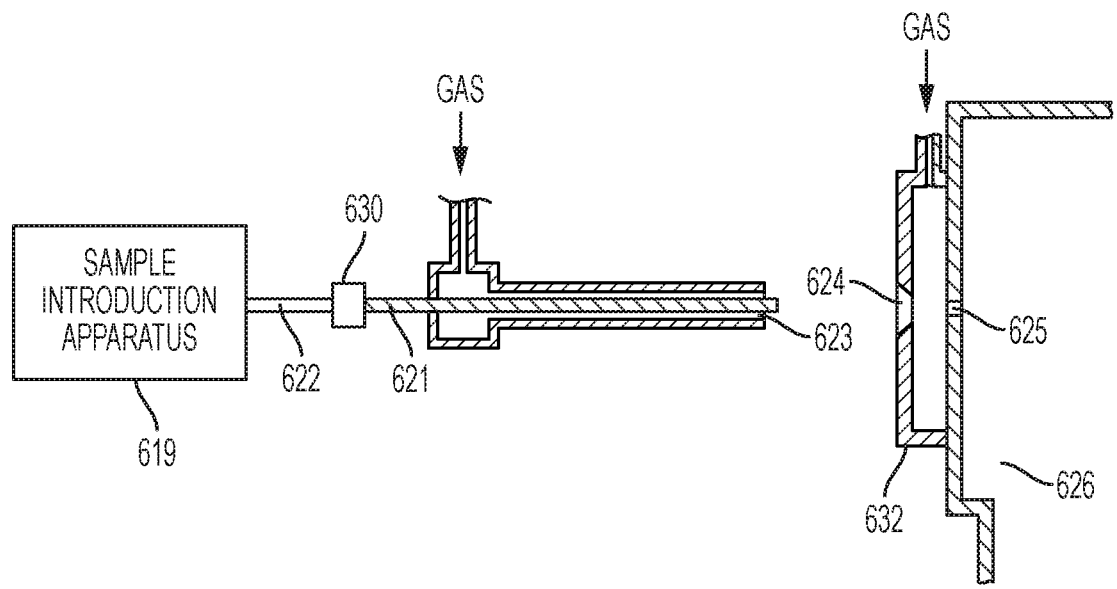
FIG. 6B shows a portion of a mass spectrometer using an electrospray method.

FIG. 6B shows a diagram of a portion of a mass spectrometer using an electrospray method. FIG. 6B is a sectional view showing the structure of a sample introduction apparatus 619 coupled to an electrospray ion source. A sample solution provided from the sample introduction apparatus 619 is introduced through a connecting tube 622 and a connector 630 into a capillary 621 for nebulization. By application of a voltage of the order of kV between the nebulization capillary 621 and a counter electrode 632, small charged droplets of the sample solution are conically nebulized from an end of the nebulization capillary, that is, a so-called electrospray phenomenon occurs. In the electrospray method, an output 623 for nebulizing gas is provided so that gas such as nitrogen gas is poured from the surroundings of the nebulization capillary 621 to thereby accelerate the vaporization of the small charged droplets. Further, the gas such as nitrogen gas is blown toward the generated small charged droplets from an outlet 624 for vaporizing gas provided in the counter electrode 632 side to thereby accelerate the vaporization of the small charged droplets. Ions thus generated are introduced through an ion sampling aperture 625 into a vacuum 626 and mass analyzed by a mass analysis region 626 under a high vacuum.

Figure 6C:
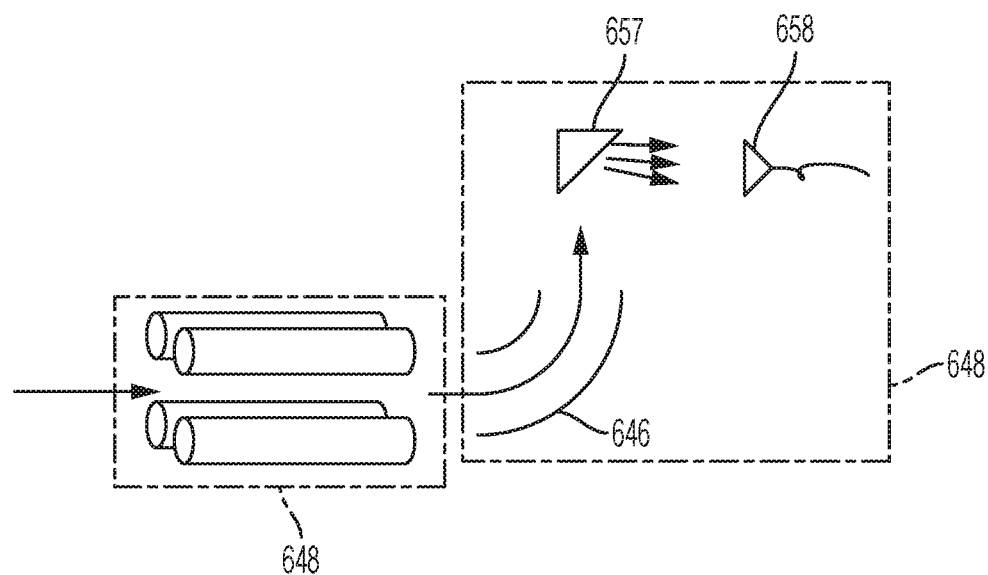
FIG. 6C shows a structure of an ion detector used in a mass spectrometer.

FIG. 6C shows a structure of an ion detector. The structure shown in FIG. 6C can be used to improve the signal-to-noise ratio (SIN) in the mass spectrometer. An ion deflecting electrode 646 can be provided in the rear portion of a mass analysis region 648 for mass separation under a high-frequency electric field to deflect mass-separated ions. The deflected ions are accelerated at a voltage of the order of kV and collide with a dynode 657 to produce secondary electrons. Secondary electrons are emitted from the secondary electron-producing dynode 657 with which the ions collide. The emitted secondary electrons are detected by an electron detector 658 such as an electron multiplier. By the structure shown in FIG. 6C, neutral molecules having no charge, charged droplets or droplets having no charge are prevented from being detected as a signal by the ion detector 648, so that improvement in S/N is attained.

As noted above, a sample introduction apparatus may be disposed between the analyzer and the mass spectrometer. One type of sample introduction apparatus can be a trap and elute apparatus. Details of a suitable trap and alute apparatus can be described with reference to FIGS. 7A and 7B.

FIG. 7A shows a diagram of components in a trap and elute apparatus 700 according to an embodiment of the invention in a first configuration. FIG. 7B shows the trap and elute system 700 according to an embodiment of the invention in a second configuration.

The trap and elute apparatus 700 includes a first pump 702 and a second pump 704, which are in fluid communication with a mixer 706. An injector 708 is downstream of and in fluid communication with the mixer 706. The injector 708 can interface with a series of valves 610. Connection points in the series of valves may be labeled 1-6. The series of valves may be present in a switching valve device 710, which may connect to a trap 712, and may connect or disconnect the trap 712 from a downstream waste station 718 or a downstream mass spectrometer 720. The trap 712 may contain any suitable material such as a C18 material.

In FIG. 7A, a sample to be processed in the mass spectrometer 720 may be pumped by pump A 702 into the mixer 706, and into the injector 708. It may then be injected into the series of valves in the switching valve device 710 (the connection points 1-2, 3-4, and 5-6 may be connected) and may flow through the trap and to the waste station. Any analyte of interest may be captured in the trap 712, and any liquid component of the sample that is not of interest may be transferred to the waste station 718.

In FIG. 7B, the connection points in the series of valves in the switching valve device 710 are switched. Now, connection points 2-3, 1-6, and 4-5 are connected. As shown, a buffer that is compatible with the mass spectrometer 720 may be pumped from the second pump 704, to the mixer 706, and to the injector 708. The injector 708 may then inject the buffer to the trap 712 and the buffer will elute any analyte of interest off of the trap 712 and into the mass spectrometer 720.

The sample processing system may be capable of performing any suitable analysis on any suitable analyte in any suitable sample. Such analyses may include immunopurification and detection processes, protein precipitation and detection processes, and SISCAPA-type processing methods. Rather than measure an intact protein directly by mass spectrometry, SISCAPA makes use of proteolytic digestion (e.g., with the enzyme trypsin) to cleave sample proteins into smaller peptides ideally suited to quantitation by mass spectrometry. By selecting a target peptide whose sequence occurs only in the selected target protein (a so-called "proteotypic" peptide), the target peptide can serve as a direct quantitative surrogate for the target protein. A synthetic version of the target peptide containing a stable isotope label can added in a known amount to the digested sample to serve as an internal standard (SIS). Since the target peptide and SIS are chemically indistinguishable throughout the workflow, but can be measured separately by a mass spectrometer due to the mass difference of the stable isotope label, their ratio provides the desired quantitative estimate of the target peptide amount.

Figure 8:
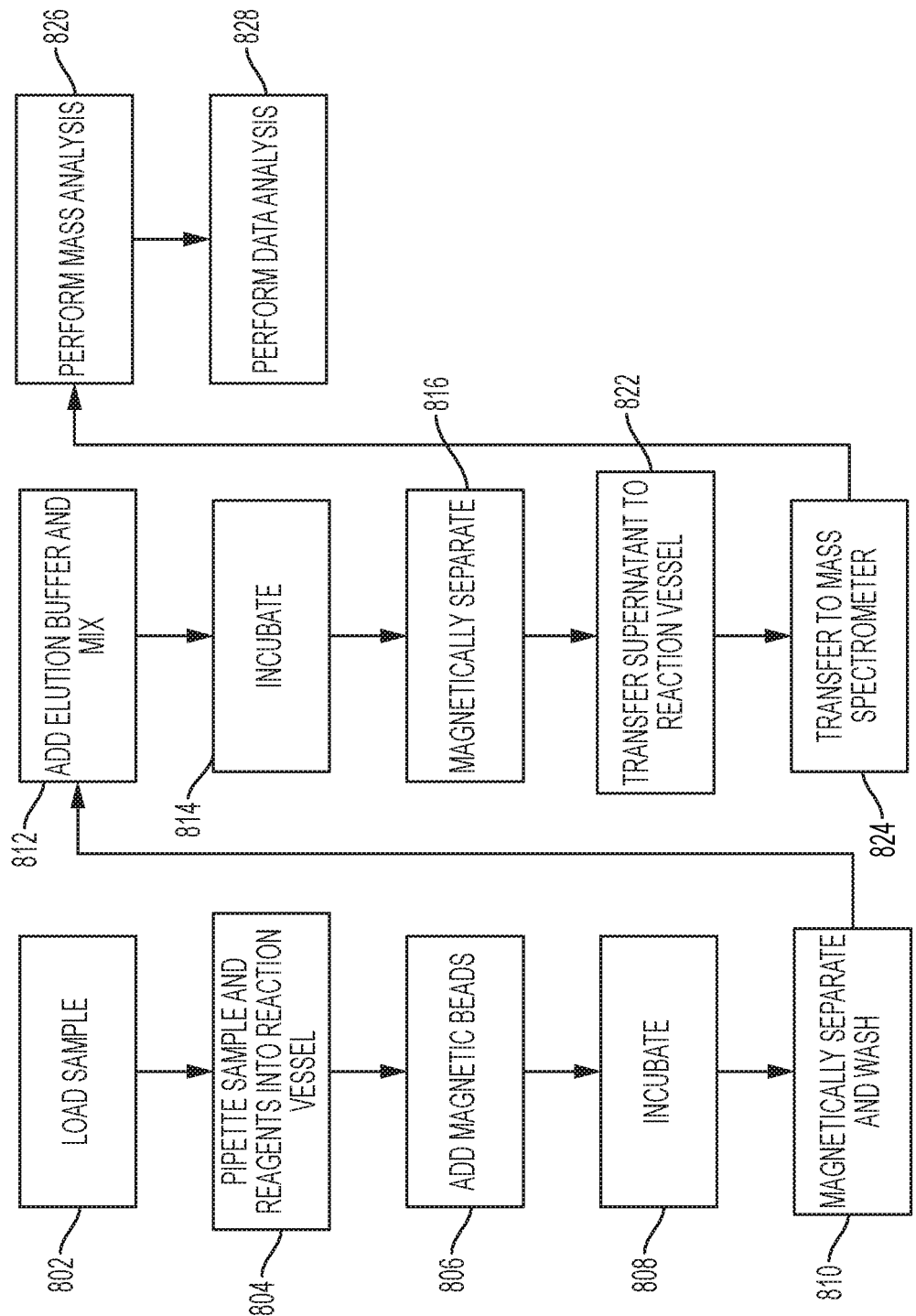
FIG. 8 shows a flowchart illustrating an immunopurification process according to an embodiment of the invention.
Figure 9:
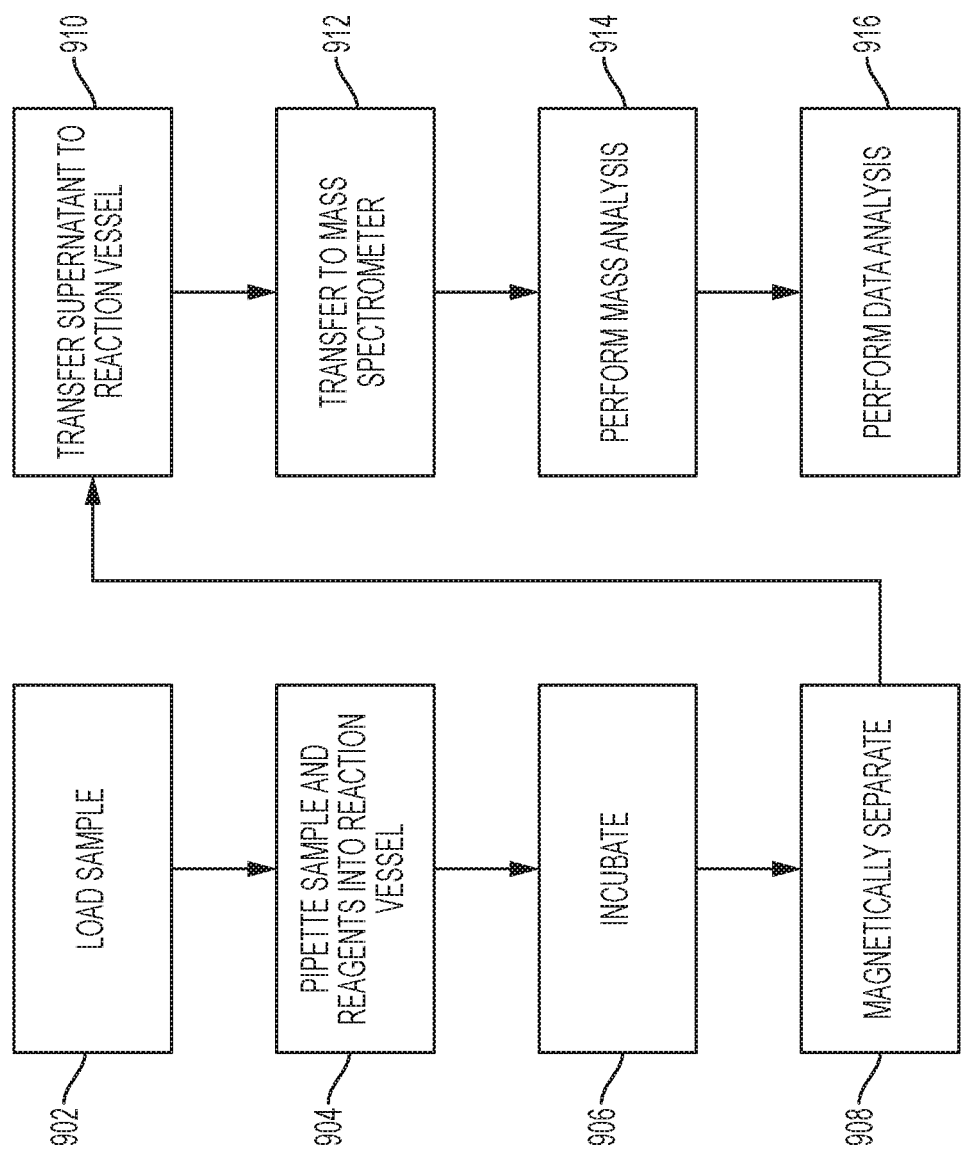
FIG. 9 shows a flowchart illustrating a protein precipitation process according to an embodiment of the invention.
Figure 10:
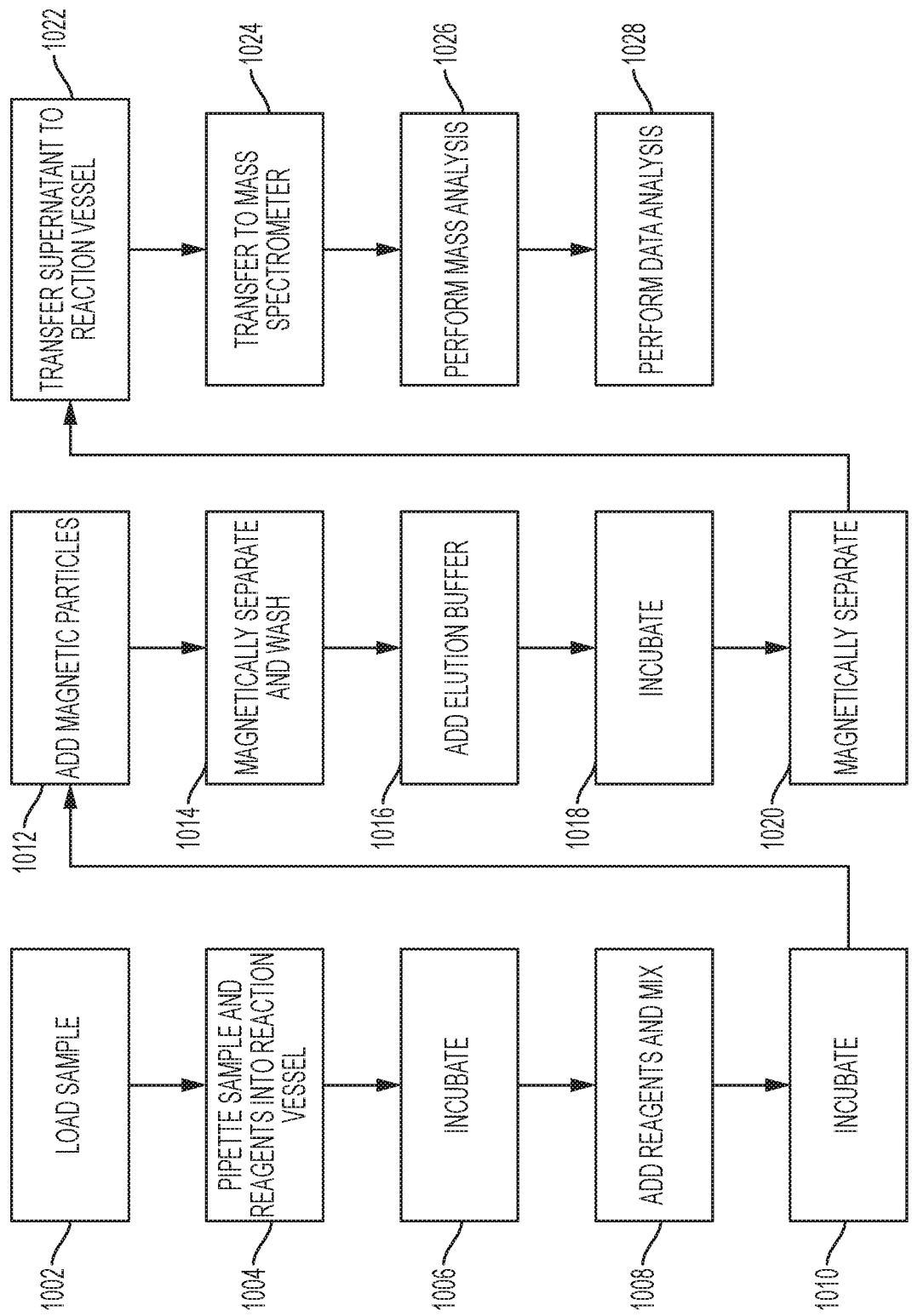
FIG. 10 shows a flowchart illustrating another immunopurification process according to an embodiment of the invention.

FIGS. 8-10 illustrate processes that utilize the analyzer to prepare a sample for a mass spectrometric analysis, and the subsequent mass analysis performed by the mass spectrometer.

FIG. 8 shows a flowchart illustrating an immunopurification process according to an embodiment of the invention. Reference can be made with respect to the analyzer diagram in FIG. 4A above.

In step 802, a sample in a sample tube is loaded into the sample presentation unit 401 in the analyzer 400. The sample tube may be present along with a number of other sample tubes in a sample tube rack or other sample tube carrier.

In step 804, the main sample pipetting station 402 may then pipette one or more aliquots of the sample in the sample tube into one or more reaction vessels provided by the bulk vessel feeder 403. At this point, the first pick and place gripper 408 may transfer the reaction vessel to the reagent pipetting stations 404, 405, 406, 407. If two sample aliquots are present in two reaction vessels, then one of the reaction vessels may be transported by the first pick and place gripper 40 to the sample storage 412 for possible future reflex testing or retesting by either the immunoanalyzer or the mass spectrometer. In some cases, a single reaction vessel with a sample aliquot may be stored in the sample storage 412 and may be used for multiple tests (e.g. by taking a secondary aliquot from the reaction vessel and transferring to a third vessel). In some cases, 5-10 tests can be run from the initial aliquot in a reaction vessel.

In step 806, in one of the reagent pipetting stations 404, 405, 406, 407, magnetic beads coated with an analyte specific capture antibody may be added to the sample aliquot in the reaction vessel along with any other suitable reagents. The reagent and the sample aliquot may then be mixed in the reagent pipetting station. Mixing can take place by using a pipettor to aspirate and dispense fluid inside of a reaction vessel repeatedly or by any other suitable mixing process. Note also that even though reagents are described as being pipetted in this and other examples, it is understood that reagents may be added to reaction vessels in any suitable manner. For example, dry reagents may be present or added to reaction vessels before or after sample aliquots are added to them.

After the appropriate reagents are added to the reaction vessel containing the sample aliquot, the second pick and place gripper 409 may transfer the reaction vessel to the incubator/wash/read station 412.

In step 808, in the incubator in the incubator/wash/read station 412, the reaction vessel containing the magnetic beads and the sample may be incubated to capture any analyte of interest on the antibodies attached to magnetic particles. The mixture in the reaction vessel may be incubated for any suitable amount of time (e.g., 60 minutes).

In step 810, in the wash apparatus in the incubator/wash/read station 412, the magnetic beads may be washed with a wash fluid, and magnetically separated from the supernatant. A pipettor in the wash apparatus can be used to dispense and remove any fluid from the reaction vessel to perform this process.

Once the washing process is completed, the second pick and place gripper 409 may then transport the reaction vessel to the reagent pipetting stations 404, 405, 406, 407. Once the analyte of interest is bound to the antibodies on the magnetic particles, the control system can determine if an immunoassay detection process or a mass spectrometric analysis process is to be performed. In some cases, the determination as to whether an immunoassay detection process or a mass spectrometric analysis process is to be performed can be made earlier in the process.

If an immunoassay detection process is to be performed, then one of the pipetting stations 404, 406, 406, 407 may dispense a chemiluminescent substrate or other optical substrate into the reaction vessel. Alternatively, the substrate can be added to the reaction vessel by a dedicated pipettor in the washing system. The reaction vessel may then be transferred by the second pick and place gripper 409 to the incubator in the incubator/wash/read station 412. In the incubator, the chemiluminescent substrate may bind to the analyte of interest, still bound to the magnetic beads. The reaction vessel may then be transferred from the incubator to the reader in the incubator/wash/read station 412 using the third pick and place gripper 410. The reader may then detect if analyte is present and/or the concentration of the analyte.

In some embodiments of the invention, the detection process may be performed by a mass spectrometer. Steps 812, 814, 816, 822, 824, 826, and 828 can be performed when a mass spectrometer is used to detect the presence or concentration of the analyte in the sample.

In step 812, instead of adding one or more optical detection reagents (e.g., a chemilumniescent substrast) into the reaction vessel, one of the reagent pipetting stations 404, 405, 406, 407 may add an elution buffer to the reaction vessel containing the processed sample. The reagent pipetting station may then mix the elution buffer with the magnetic particles including the bound analyte. After this step has been performed, the second pick and place gripper 409 may then transfer the reaction vessel to the incubator in the incubator/wash/read station 412.

In step 814, in the incubator, an incubation process may be performed in the incubator in the incubator/wash/read station 412. The mixture in the reaction vessel may be incubated for any suitable period of time.

In step 816, a magnetic separation process can be performed in a wash station in the incubator/wash/read station 412 to separate the supernatant from the magnetic particles. Alternatively, as noted above, a magnetic separation process can be performed in the incubator in the incubator/wash/read station 412 if the incubator includes incubation regions with magnets. In other case, a magnet in either the wash station or the incubator in the incubator/wash/read station 412, or even in one of the pipetting stations 404, 405, 406, 407 may allow confine the magnetic particles to a location in the reaction vessel.

In step S822, the supernatant containing the analyte of interest in the reaction vessel may be transferred to a second reaction vessel using pipettor proximate to the incubator/wash/read station, or at any other suitable location, leaving behind the magnetic particles in the first reaction vessel.

In step 824, the second reaction vessel or the supernatant containing the analyte of interest may be transferred to the mass spectrometer using one or more of sample introduction apparatuses.

If desired, at this point in the process, one or more mass tags or derivativing agents may be added to the supernatant containing the analyte of interest. The mass tags or derivatizing agent can be added by one of more of the reagent pipetting stations 404, 405, 406, 407.

In step 826, once the supernatant containing the analyte of interest is in the mass spectrometer, a mass analysis can be performed.

In step 828, a data analysis may be performed by the mass spectrometer, as described above.

FIG. 9 shows a flowchart illustrating a protein precipitation process according to an embodiment of the invention. In a protein precipitation process, proteins in a sample that are not of interest can be bound to magnetic particles. The magnetic particles may be separated from a supernatant containing the analyte of interest in a reaction vessel. The analysis illustrated in FIG. 9 can be performed instead of an immunoassay process or as a reflex test for a prior immunoassay process.

In step 902, a sample in a sample tube is loaded into the sample presentation unit 401 in the analyzer 400. The sample tube may be present along with a number of other sample tubes in a sample tube rack or other sample tube carrier.

In step 904, the main sample pipetting station 402 may then pipette a mixture of an aliquot of the sample, assay standard, and precipitation buffer containing paramagnetic microparticles into the reaction vessel provided by the bulk vessel feeder 403. The mixture in the reaction vessel may then be mixed at the main sample pipetting station using multiple dispense and aspiration steps, or using any other suitable mixing process.

At this point, the second pick and place gripper 409 may transfer the reaction vessel to the incubator/wash/read station 412.

In step 906, in the incubator in the incubator/wash/read station 412, the reaction vessel containing the mixture may be incubated, so that any protein matrix within the sample aliquot is bound to the paramagnetic microparticles.

In step 908, in the wash apparatus in the incubator/wash/read station 412, the paramagnetic microparticles with the bound protein matrix magnetically separated from the supernatant containing the analyst of interest. Alternatively, as noted above, a magnetic separation process can be performed in the incubator in the incubator/wash/read station 412 if the incubator includes incubation regions with magnets.

In step 910, the supernatant containing the analyte of interest in the reaction vessel may be transferred to a second reaction vessel provided by the bulk vessel feeder 403 using a pipettor proximate to the incubator/wash/read station 412.

In step 914, once the supernatant containing the analyte of interest is in the mass spectrometer, a mass analysis can be performed.

In step 916, a data analysis may be performed by the mass spectrometer.

In some embodiments, instead of performing steps 908, 910, and 912, the analyzer could transfer the reaction vessel to a centrifuge module (which may be located in the analyzer, the mass spectrometer, or may be separate from them), spun, and then returned to the analyzer.

FIG. 10 shows a flowchart illustrating another immunopurification process according to an embodiment of the invention. The process illustrated in FIG. 10 may be a SISCAPA-type processing method as described above.

In step 1002, a sample in a sample tube is loaded into the sample presentation unit 401 in the analyzer 400. The sample tube may be present along with a number of other sample tubes in a sample tube rack or other sample tube carrier.

In step 1004, the main sample pipetting station 402 may then pipette an aliquot of the sample in the sample tube, and a denaturing reagent/alkalynating reagent, into a reaction vessel provided by the bulk vessel feeder 403. The first pick and place gripper 408 may then transfer the reaction vessel to the incubator in the incubator/wash/read station 412 so that an incubation process can be performed.

In step 1006, the reaction vessel containing the sample is incubated.

After incubation, the second pick and place gripper 409 may transfer the reaction vessel to the reagent pipetting stations 404, 405, 406, 407.

In step 1008, one of the reagent pipetting stations 404, 405, 406, 407 may add trypsin and may mix the resulting mixture in the reaction vessel. The second pick and place gripper 409 may then transfer the reaction vessel to the incubator in the incubator/wash/read station 412.

In step 1010, in the incubator, an incubation process may be performed in the incubator of the incubator/wash/read station 412. At this point, the second pick and place gripper 409 may transfer the reaction vessel to one of the reagent pipetting stations 404, 405, 406, 407.

In step 1012, one of the reagent pipetting stations 404, 405, 406, 407 may add magnetic microparticles coated with antibodies and SIS peptides. After this step has been performed, the second pick and place gripper 409 may then transfer the reaction vessel to the incubator in the incubator/wash/read station 412.

In step 1014, in the wash apparatus in the incubator/wash/read station 412, a magnetic separation and wash process may be performed. Once this process step has been performed, the second pick and place gripper 409 may then transport the reaction vessel to the reagent pipetting stations 404, 405, 406, 407.

In step 1016, one of the reagent pipetting stations 404, 405, 406, 407 may add an elution buffer and may then mix the elution buffer with the magnetic particles including the bound analyte. After this step has been performed, the second pick and place gripper 409 may then transfer the reaction vessel to the incubator in the incubator/wash/read station 412.

In step 1018, in the incubator, an incubation process may be performed in the incubator in the incubator/wash/read station 412.

In step 1020, a magnetic separation process can be performed in a wash station in the incubator/wash/read station 412. Alternatively, as noted above, a magnetic separation process can be performed in the incubator in the incubator/wash/read station 412 if the incubator includes incubation regions with magnets.

In step 1022, the supernatant containing the analyte of interest in the reaction vessel may be transferred to a second reaction vessel using pipettor proximate to the incubator/wash/read station.

In step 1024, the second reaction vessel or the supernatant containing the analyte of interest may be transferred to the mass spectrometer using one or more sample introduction apparatuses.

In step 1026, once the supernatant containing the analyte of interest is in the mass spectrometer, a mass analysis can be performed.

In step 1028, a data analysis may be performed by the mass spectrometer.

The sample processing systems and methods disclosed herein can be used to improve the quality and efficiency of a variety of tests to benefit patients. The following are non-limiting examples.

Drugs of Abuse

In some embodiments, the sample processing system can be used to process a biological sample according to a test order to detect one or more drugs of abuse in a patient. The drug of abuse may be one that is selected from the group consisting of: alcohol, amphetamines, benzoylecgonine, opiates, barbiturates, morphine, benzodiazepines, cocaine, marijuana, methadone, methamphetamines, tetrahydrocannabinol, hydrocodone, hydromorphone, oxycodone, codeine, 6-monoacetylmorphine, meperidine, phencyclidine propoxyphene, oxymorphone, fentanyl, and phencyclidine (PCP).

Bodily fluid samples can be collected from the patient for the test. Suitable examples of bodily fluid include, but not limited to, blood, saliva, sweat, and urine. The samples can then be prepared, and appropriate analyzer(s) can be determined using the above-described condition sets and parameters. For example, a condition set may determine that a particular biological sample is to be analyzed using a mass spectrometer. The biological sample is then prepared according to a standard mass spectrometry sample preparation procedure. Prepared samples can then be introduced into a mass spectrometer and the amounts of each of the one or more drugs of abuse and their metabolites can be measured. Each of the measurements can be compared with a predetermined reference range, which corresponds to the levels of the drug in individuals who do not abuse, if the measurement is greater than the upper limit of the respective reference, the patient is determined to have abused the drug. Optionally, the system may generate a report of patient compliance or abuse based on the comparison. In a more specific example, for drugs of abuse, an order could be to test for a drug of abuse such as an opioid. Since the clinical value can be extremely low—the system would then the suggest using a mass spectrometer.

Therapeutic Drug Monitoring

In some embodiments, the sample processing system can be used to process a biological sample according to a test order to monitor a patient's compliance with his or her prescription of a therapeutic drug. Typically the patient's prescription record is stored in the patent information in the information management apparatus, which may including an HIS or LIS. A bodily fluid sample can be periodically collected from the patient who is taking a prescription drug and analyzed using a mass spectrometer or other analyzer. The specific analyzers may be selected based upon the above described test order, condition sets, and parameters. The drug or the metabolites thereof in each of the samples can be detected, quantified, and compared with the patient's prescription record to monitor whether the patient is take the prescribed drug in the prescribed amounts. For example, a detected amount that is above the upper limit of the reference range indicates that the patient has been overdosed and a detected amount that is below the lower limit of the reference range indicates that the patient has not taken the drug in sufficient amount and/or frequency.

One particular category of therapeutic drugs is immunosuppressant drugs, which are typically given to organ transplant patients to prevent transplant rejection. Immunosuppressant drugs require close monitoring because of their narrow therapeutic index and significant inter-individual variability in blood concentrations. This variability is typically due to factors such as drug-nutrient interactions, drug-disease interactions, renal-insufficiency, inflammation and infection, gender, age, polymorphism and liver mass. Suitable immunosuppressant drugs can be measured using the sample processing system of the invention include, but are not limited to, cyclosporine, tacrolimus, sirolimus and mycophenolic acid. In some cases, the method further comprises comparing the measurement value with a reference range that is deemed to be safe for organ transplant and determining organ transplant can be performed if the measurement value is within a predetermined reference range, or determining that additional amount of the immunosuppressant needs to be administered if the measurement values are lower than the lower limit of the reference range.

Steroids

In some embodiments, the sample processing system can be used to process a biological sample according to a test order to determine whether or not a biological sample of a patient contains steroids at a particular concentration. For example, one may wish to determine if a patient is pregnant. This typically involves testing pregnancy-related hormones, such as luteinizing hormone (LH) and human chorionic gonadotropin (hCG).

In a female, LH secretion induces ovulation of mature follicles and leads to secretion of estradiol and progesterone, which is necessary for maintenance of pregnancy. HCG is typically produced 6-7 days after fertilization occurs and continues to rise during pregnancy and can be used to determine the stage of the pregnancy. Thus, the hCG levels in blood and comparison with a reference value can be used to determine pregnancy status. In some cases, the testing of the pregnancy-related hormones can be assayed simultaneously with the Down syndrome panel, as described below. In some cases, the testing of pregnancy could be assayed simultaneously with other tests if the age of the mother was above a threshold—for example, if the mother is older than 35. The system could also analyze the sample for Down's syndrome (for example using a Molecular Biology analyzer). Or if the mother has a history of having taken a drug known to cause birth defects, the sample could be similarly be tested.

In some embodiments, the system and methods disclosed herein can be used to determine whether the fetus has Down syndrome by assaying a panel of analytes. The Down syndrome panel of analytes typically include alpha-fetoprotein (AFP), estriol, human chorionic gonadotropin, inhibin A, and pregnancy-associated plasma protein-A (PAPP-A). When the fetus has Down syndrome, the AFP and estriol levels are decreased, while the beta unit of the hCG and inhibin A are increased in blood. The Down syndrome panel is typically determined during the second trimester of pregnancy. Thus, the disclosure provides a system to determine the whether the fetus has Down syndrome by obtaining a blood sample from the patient and assaying the amount of analytes including alpha-fetoprotein (AFP), estriol, human chorionic gonadotropin, inhibin A, and pregnancy-associated plasma protein-A (PAPP-A) using the system described above. A detection of inhibin A and a beta unit of the human chorionic gonadotropin levels above respective reference levels, and a detection of AFP and estriol levels below their respective reference levels indicate the fetus has Down's syndrome.

The various analyzers in the sample processing system can be used to test for the presence of steroids in a biological sample. The specific analyzers may be selected based upon the above described test order, condition sets, and parameters.

Vitamin D

In some embodiments, the sample processing system can be used to process a biological sample according to a test order to detect vitamin D in the biological sample. Monitoring a vitamin D amount in body is desirable: on one hand, vitamin D deficiencies can have devastating consequences on bone development, immune function and cancer prevention; on the other hand, vitamin D toxicity resulting from over medication can cause hypercalcemia, which is often accompanied with symptoms of stomach upset, nausea, vomiting and constipation. Hypercalcemia can also weaken the bones and create kidney stones.

Vitamin D has two bioequivalent forms: vitamin D2, which are obtained from vegetable sources, and vitamin D3, which are derived from endogenous sources (synthesized from cholesterol through sun exposure) and exogenous sources (animal diet). Vitamin D exists in the body mainly in the form of 25-hydroxyvitamin D and thus the amount of 25-hydroxyvitamin D corresponds to the amount of vitamin D the body stores. The total amount of 25-hydroxyvitamin D is the sum of 25-hydroxyvitamin D2 and 25-hydroxyvitamin D3. In some cases, 25-hydroxyvitamin D2 and 25-hydroxyvitamin D3 levels are also separately assessed, which allows identification of the source of the deficiency and prescribing treatment. For example, a low level of 25-hydroxyvitamin D2 may indicate that the patient would benefit from increasing vegetable intake.

The reference value for vitamin D, i.e., normal amount of vitamin D is typically within the range of 25-80 ng/mL. A detection of an amount that is lower than 25 ng/mL thus may indicate vitamin D deficiency and an amount that is higher than 80 ng/mL may indicate the excessive vitamin D. Physicians can prescribe treatment accordingly based on the information.

The various analyzers in the sample processing system can be used to test for the presence of vitamin D in a biological sample. The specific analyzers may be selected based upon the above described test order, condition sets, and parameters.

Sepsis

In some embodiments, the sample processing system can be used to process a biological sample according to a test order to diagnose sepsis. Sepsis develops when the immune system releases certain chemicals into the bloodstream to fight an infection, which cause inflammation throughout the entire body. Severe cases of sepsis can lead to septic shock, a life-threatening condition. Detection of sepsis provides clinicians valuable information to determine whether antibiotics should be immediately administered in certain situations when the patient is especially vulnerable for infection, such as during or after surgery.

Sepsis is typically diagnosed based on one or more of the analytes selected from the group consisting of C-reactive protein (CRP), interleukin-6 (IL-6), and procalcitonin. Normal CRP ranges in blood may be less than 10 mg/l; levels of 10 to 50 mg/l indicate an infection with low or medium impact likely caused by a local infection; and levels of 50 to 100 mg/l indicate a high infection with a root cause analysis and immediate attention required. In addition, IL-6 activates increasing leucocyte population in the blood count and can forewarn of an upcoming infection even before the fever of the patient is detected by the clinician. The test results of the IL-6 and procalcitonin tests are useful to distinguish between a bacterial infection and an autoimmune reaction due to a chronic disease—in the case of a bacterial inflammation the procalcitonin value increases, while in the case of a viral infection the procalcitonin value is mostly in the normal range. Thus, a comparison of the measurements of these markers with respective reference ranges can be used to diagnose sepsis and also to identify the source of infection, thus allowing clinicians to provide proper treatment to the patient.

The various analyzers in the sample processing system can be used to test for the presence of analytes that may be indicative of sepsis in a biological sample. The specific analyzers may be selected based upon the above described test order, condition sets, and parameters.

For sepsis, in some embodiments, a MDW score on a hematology unit would result in the system using an immunoassay analyzer (IA) or MS (mass spectrometer) to test for PCT, IL6, IL8 levels—or directing sample to be cultured and then tested on a microbiology system. Or, one could first test for high PCT, and then send to the hematology unit for the MDW score. Another case would be that where a patient has recently had surgery; if the clinician notes inflammation—then test for PCT and MDW to rule out sepsis.

In some embodiments, the sample processing system can be used to process a biological sample according to a test order to diagnose Alzheimer's disease. Tests can be typically performed on cerebrospinal fluid (CSF), plasma, saliva, or whole blood samples collected from the patient to analyze one or more protein/steroid markers such as phosphorylated-Tau protein, total Tau protein, CSF amyloid beta (1-42), C-reactive proteins, homocysteine, alpha-synuclein, neuron-specific enolase (NSE), and dehydroepiandrosterone sulfate. A patient having Alzheimer's disease typically has increased amounts in one or more of the aforementioned markers as compared to controls. In some cases, a decrease in circulating miRNAs, such as miR-125b, miR-23a, and miR-26b, and/or an increase in the amount of reactive oxygen species (ROS) can also be used to diagnose Alzheimer's disease. See Galimberti et al., *Circulating miRNAs as potential biomarkers in Alzheimer's disease*, J. Alzheimer's Dis. 2014; 42(4): 1261-7.; Huang et al. *Role of oxidative stress in Alzheimer's disease*, Biomed. Rep. 2016 May; 4(5): 519-522.

Alzheimer's Disease

In some embodiments, the sample processing system can be used to process a biological sample according to a test order to diagnose Alzheimer's disease. Tests can be typically performed on cerebrospinal fluid (CSF), plasma, saliva, or whole blood samples collected from the patient to analyze one or more protein/steroid markers such as phosphorylated-Tau protein, total Tau protein, CSF amyloid beta (1-42), C-reactive proteins, homocysteine, alpha-sunuclein, neuron-specific enolase (NSE), and dehydroepiandrosterone sulphate. A patient having Alzheimer's disease typically has increased amounts in one or more of the aforementioned markers as compared to controls. In some cases, a decrease in circulating miRNAs, such as miR-125b, miR-23a, and miR-26b, and/or an increase in the amount of reactive oxygen species (ROS) can also be used to diagnose Alzheimer's disease. See Galimberti et al., *Circulating miRNAs as potential biomarkers in Alzheimer's disease*, J. Alzheimer's Dis. 2014; 42(4): 1261-7.; Huang et al. *Role of oxidative stress in Alzheimer's disease*, Biomed. Rep. 2016 May; 4(5): 519-522.

Thus, the disclosure provides sample processing systems and methods for determining whether a patient has Alzheimer's disease by obtaining a bodily fluid sample, such as cerebrospinal fluid (CSF), plasma, saliva, or whole blood, from the patient, and assaying the amount of one or more of the following analytes: phosphorylated-Tau protein, total Tau protein, CSF amyloid beta (1-42), C-reactive proteins, homocysteine, alpha-synuclein, neuron-specific enolase (NSE), and dehydroepiandrosterone sulfate, miR-125b, miR-23a, and miR-26b, and ROS. The results may be compared with reference values stored in the control system and a diagnosis can be made based on the comparison as described above.

The various analyzers in the sample processing system can be used to test for the presence of analytes that may be indicative of Alzheimer's disease in a biological sample. The specific analyzers may be selected based upon the above described test order, condition sets, and parameters.

Cardiac Disease and Stroke

In some embodiments, the sample processing system can be used to process a biological sample according to a test order to detect the risk of having cardiac disease or a stroke. Many forms of cardiovascular diseases begin with atherosclerosis, a condition where the arteries become hardened and narrowed due to plaque build-up around the artery wall. Plaque made of cholesterol, fatty substances, cellular waste products, calcium and fibrin may partially or totally block the blood's flow through an artery in the heart, brain, pelvis, legs, arms or kidneys. This blockage may develop into serious diseases, such as coronary heart disease, chest pain, carotid artery disease, peripheral artery disease (PAD) and chronic kidney disease. Even worse, if a piece of the plaques breaks off or a blood clot (thrombus) forms on the plaque's surface, a heart attack or stroke may result.

A number of lipoprotein markers are good biomarkers for cardiac disease and can be measured from bodily fluid samples collected from the patient, e.g., blood, plasma, serum using the mass spectrometer. These markers include B-type natriuretic peptide (BNP), proBNP (a non-active prohormone that produces BNP), human C-reactive protein (hs-CRP) and pregnancy associated plasma protein-A (PAPP-A). Many of these natriuretic peptides can aid in determination of plaque progression and risk of onset of stroke. Other markers include triglyceride to HDLp (high density lipoproteins) ratio, lipophorin-cholesterol ratio, lipid-lipophorin ratio, LDL cholesterol level, HDLp and apolipoprotein levels, lipophorins and LTPs ratio, sphingolipids, Omega-3 Index, and ST2 levels, which can be assayed using the mass spectrometer of the system. The measurements can be compared with reference ranges according to pre-stablished rules to determine the risk of cardiac disease or stroke.

The various analyzers in the sample processing system can be used to test for the presence of analytes that may be indicative of cardiac disease and/or stroke in a biological sample. The specific analyzers may be selected based upon the above described test order, condition sets, and parameters.

Cancer

The present sample processing system can also be used to detect various cancers. Cancer typically refers to the physiological condition in mammals that is typically characterized by unregulated cell growth and/or proliferation. Patients who developed particular cancers may show notable differences in levels of cancer-specific markers, in blood, serum, plasma or other bodily fluid as compared to healthy individuals. However, as with other tests, a single marker on its own often is not specific or sensitive enough to diagnose cancers, especially those that are still in early stages. The systems and methods disclosed herein are especially advantageous in that they can be utilized to test a panel of biomarkers, which collectively, can be used to detect the presence of the cancer with high accuracy. The cancer-specific biomarkers may include protein markers and DNA markers. In some cases, the protein markers detection is combined with DNA markers detection method to further increase the assay sensitivity and specificity. The samples can be analyzed using a mass spectrometer in the system to detect and/or quantifying the amount of the protein markers. In some cases, the samples are further analyzed using an immunoanalyzer to confirm the identity of the protein markers. In other cases, the samples are further analyzed using a molecular biology analyzer of the system to further assess the DNA markers. The measurements of these cancer-specific markers can be compared with reference ranges according to pre-stablished rules to detect the presence of and/or stage of cancer. A few specific cancers are discuss below as illustrative examples.

In some embodiments, the sample processing system can be used to process a test order for detecting breast cancer. In general, relative to healthy individuals, breast cancer patients have a higher average concentration of insulin-like growth factor-1 (IGF-1), IGF-2, IGF-binding protein 2 (IBP2), IBP3 and leucine-rich a-2-glycoprotein (A2GL), Erbb2/HER2, osteopontin, enolase 1 (ENO1), PKM2 and LDHA and/or fibulin-2. Thus detecting an increase in one or more of these markers may indicate the patient has breast cancer. Once diagnosed with breast cancer, the subject can also be periodically tested for the plasma levels of fibronectin, clusterin, gelsolin and a-1 microglobulin/inter-a-trypsin inhibitor light chain precursor (AMBP), an increase of one or more of these markers generally indicates an advancement of the breast cancer.

In some embodiments, the sample processing system can be used to process a test order for detecting colorectal cancer. In colorectal cancer patients, adenosylhomocysteinase (AHCY), cathepsin D (CTSD), S100A9 and lysozyme C (LYZ) are increased relative to healthy individuals and the amount of these markers in colorectal cancer blood samples across the four stages of colorectal cancer are known. In addition, collagen a-1 (I) chain (COL1A1) and maltase-glucoamylase (MGAM) are decreased and inter-a trypsin inhibitor heavy chain H3 (ITIH3) and coagulation factor V (F5) are increased relative to controls. The mass spectrometer of the system can be used to detect one or more the markers above and result can be used to diagnose colorectal cancer. Advantageously, a mass spectrometer can detect differences in structural sugar compositions; this is crucial for diagnosis of invasive and metastatic colon cancer as aberrant glycoforms of both tissue inhibitor of metalloproteinase 1 (TIMP1) and protein tyrosine phosphatase k (PTPk) are typically higher than the patients who do not have these aggressive forms of colon cancers.

In some embodiments, the sample processing system can be used to process an test order for detecting prostate cancer. In prostate cancer patients, PSA and its post-translationally modified forms along with the sialylated forms of PSA are increased as compared to healthy individuals. In addition, the presence of N-acylethanolamine acid amidase and protein tyrosine kinase 7 has been shown to be significantly associated with aggressive prostate cancer. Further vinculin and galectin-3 have been shown to be urinary biomarkers for recurrent prostate cancer. Thus, the system can be used to detect prostate cancer by assaying one or more of the markers above to diagnose prostate cancer.

In some embodiments, the sample processing system can be used to process a test order for detecting ovarian cancer. In ovarian cancer patients, a panel of analytes comprising CLIC1, CLIC4, TPM1, TPM2, TPM3, TPM4, and inhibin have been shown to be significantly up-regulated in ovarian cancer in comparison to healthy controls and thus one or more of the above markers can be detected using the analyzers of the system. In preferred embodiments, the panel to be tested comprise all six aforementioned analytes. In some cases, the panel of analytes to be tested can further include CA 125. In addition, the system and method disclosed herein can also be used to distinguish benign ovarian tumors versus malign ovarian tumors by testing panels of beta-2-microglobulin, ApoA1, transthyretin and transferrin—these analytes show significant increase in serum samples in subjects with benign ovarian tumors as compared to patients having malign ovarian tumors.

In some embodiments, the sample processing system can be used to process a test order for detecting lung cancer. Lung cancer is one of the most common cancer diseases with very poor prognosis and high mortality. A number of biomarkers have been reported to associate with lung cancer, such as CEA, AGP, neuron-specific enolase (NEA), however these biomarkers lack the desired sensitivity and specificity. Recently, other markers such as sialylated (SAA) isoforms SAA1 and SAA2, haptoglobin (Hp) subunits (mostly a chain), a-1B-glycoprotein (A1BG) and leucine-rich a-2-glycoprotein (LRG1), are shown to be elevated in sera from lung cancer patients as compared to controls. Other useful markers that can be detected are zyxin and CD109, the up-regulation of which indicate lung cancer progression and toward metastatic late stage. Thus, in some embodiments, the present system is used to detect and/or measure one or more biomarkers selected from the group consisting of are sialylated (SAA) isoforms SAA1 and SAA2 levels, haptoglobin (Hp) subunits (mostly a chain), a-1B-glycoprotein (A1BG) and leucine-rich a-2-glycoprotein (LRG1), zyxin, and CD109. The measurements can then be compared with respective reference values to determining the presence and the stage of lung cancer according established correlations between the amounts of these markers and status of the disease.

In some embodiments, the sample processing system can be used to process a test order for detecting pancreatic cancer. Pancreatic cancer is the fourth leading cause of cancer—related death in the United States. CA19-9 is one of the markers who have been found to be upregulated and such upregulation can be detected in blood samples of the patients. However, in some cases detection of CA19-9 sensitivity is low and detection of additional biomarkers such as a-fibrinogen-containing hydroxylated proline and serotransferrin peptide in bodily fluid sample, such as blood or serum, are necessary to improve assay accuracy. The levels of these markers are typically increased in patients bearing pancreatic cancer in comparison with healthy controls. In addition, an increase in the levels of transforming growth factor beta-induced (TGFBI), later transforming growth factor beta binding 2 (LTBP2) and/or asporin (ASP) as compared to controls can be used to diagnose pancreatic ductal adenocarcinoma (PDAC).

In some embodiments, the sample processing system can be used to process a test order for detecting bladder cancer. Bladder cancer is the most common carcinoma of the urinary tract. Biomarkers including the CD44 antigen, clusterin, adiponectin, afamin, ApoA-II precursor, CERU, complement C4 gamma chain and prothrombin; measuring one or more of these markers in suitable bodily fluid samples may be used to diagnose bladder cancer.

Hepatocellular cancer is the second leading cause of cancer-related death worldwide due to latent liver disease and late diagnosis. A number of N-glycoproteins, such as AGP, CERU, a-HS-glycoprotein, kininogen-1 and carboxypeptidase B2, are increased more than 2.5-fold in liver cancer patients relative to controls. Other markers include APF, actin binding-protein aniline (ANLN), filamin B (FLNB) and complementary C4-A (C4A). Thus, in some cases, the system is configured to measure the levels of one or more biomarkers selected from the group consisting of AGP, CERU, a-HS-glycoprotein, kininogen-1 and carboxypeptidase B2, APF, ANLN, FLNB, and C4A, and measurements of one or more of these biomarkers to determine the presence of hepatocellular cancer.

In addition the aforementioned types of cancer, other types of cancer can be similarly diagnosed by measuring biomarkers that are specific to that cancer using the systems and methods disclosed herein. Non-limiting examples of the types of cancer include, carcinoma, lymphoma (e.g., Hodgkin's and non-Hodgkin's lymphoma), blastoma, sarcoma, and leukemia. More particular examples of such cancers can include squamous cell cancer, small-cell lung cancer, non-small cell lung cancer, adenocarcinoma of the lung, squamous carcinoma of the lung, cancer of the peritoneum, gastrointestinal cancer, pancreatic cancer, glioblastoma, cervical cancer, liver cancer, bladder cancer, hepatoma, cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The various analyzers in the sample processing system can be used to test for the presence of analytes that may be indicative of cancer in a biological sample. The specific analyzers may be selected based upon the above described test order, condition sets, and parameters.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

All patents, patent applications, publications, and descriptions mentioned above are herein incorporated by reference in their entirety.

What is claimed is:

1. A sample processing system for analyzing a biological sample from a patient, the sample processing system comprising:
   a plurality of analyzers comprising at least one mass spectrometer, wherein each analyzer in the plurality of analyzers is configured to acquire at least one measurement value related to at least one characteristic of the biological sample;
   at least one data storage component which stores (i) a list of parameters for the plurality of analyzers, and (ii) at least two condition sets, which contain data associated with completing one or more test orders, wherein the at least two condition sets contain data which differ by at least one variable; and
   a control system operatively coupled to the plurality of analyzers, and the at least one data storage component, and wherein the control system comprises a data processor and a computer readable medium, the computer readable medium comprising code, executable by the data processor to (i) determine which condition set of the at least two condition sets to use, (ii) determine which analyzer or analyzers of the plurality of analyzers to use to process the one or more test orders based on the determined condition set and one or more parameters from the list of parameters, and (iii) cause the determined analyzer or analyzers to acquire one or more measurement values for the biological sample.

2. The sample processing system of claim 1, wherein a condition set in the at least two condition sets includes a variable that includes a parameter of an analyzer that includes a detection range of the analyzer.

3. The sample processing system of claim 1, wherein for a test order to test for at least one drug or metabolite thereof or both, at least one condition set of the at least two condition sets causes the control system to determine the mass spectrometer from the plurality of analyzers.

4. The sample processing system of claim 3, wherein the sample processing system further comprises an information management apparatus configured to compare a presence or absence of a drug or metabolite thereof as determined from measurement values from the mass spectrometer to any medications in patient information in a patient information repository.

5. The sample processing system of claim 3, wherein the drug is a therapeutic drug.

6. The sample processing system of claim 3, wherein the drug is a drug of abuse.

7. The sample processing system of claim 3, wherein the drug is an immunosuppressant drug.

8. The sample processing system of claim 1, wherein for a test order to test for vitamin D, at least one condition set of the at least two condition sets selects the determined analyzer to be the mass spectrometer.

9. The sample processing system of claim 1, wherein for a test order to test for a protein marker or lipid marker, at least one condition set of the at least two condition sets selects the determined analyzer to be the mass spectrometer.

10. The sample processing system of claim 9, wherein expression of the protein marker or lipid marker correlates to a disease.

11. The sample processing system of claim 1, wherein the variable in the condition set is from patient information of a patient associated with the biological sample.

12. The sample processing system of claim 11, wherein the variable is an age or sex of a patient associated with the biological sample.

13. The sample processing system of claim 11, wherein for a test order to test for a steroid, at least one condition set selects the determined analyzer to be the mass spectrometer.

14. The sample processing system of claim 13, wherein the steroid is testosterone, estradiol or progesterone.

15. The sample processing system of claim 11, wherein the variable is insurance coverage of a patient associated with the biological sample.

16. The sample processing system of claim 11, wherein the variable is a predetermined value set by a laboratory.

17. The sample processing system of claim 1, wherein the computer readable medium of the control system further comprises code executable by the data processor to cause a transport system to route the biological sample to the determined analyzer or analyzers.

18. The sample processing system of claim 1, wherein the computer readable medium of the control system further comprises code, executable by the data processor, to determine which analyzer or analyzers to use also based on a list of available analyzers.

19. The sample processing system of claim 1, further comprising:
   an information management apparatus coupled to the control system, and being configured to (i) store patient information, (ii) receive one or more test orders for the biological sample, and (iii) receive the one or more measurement values of the biological sample from the plurality of analyzers.

20. A method performed by a system comprising a plurality of analyzers comprising at least one mass spectrometer, at least one data storage component storing a plurality of condition sets, the condition sets in the plurality of condition sets differing by at least one variable, and a plurality of parameter lists for the plurality of analyzers, and a control system coupled to the plurality of analyzers, and the at least one data storage component, the method comprising:
   determining, by the control system, in response to receipt of a test order to test a biological sample, one or more condition sets of the plurality of condition sets in the data storage component to use to complete the test order;
   determining, by the control system, an analyzer or analyzers from the plurality of analyzers to use to process the biological sample based on the one or more condition sets, and one or more parameter lists in the plurality of parameter lists, the determined analyzer or analyzers including the at least one mass spectrometer; and
   causing, by the control system, the determined analyzer or analyzers of the plurality of analyzers to process the biological sample to determine one or more measurement values for the biological sample.

* * * * *